US012285413B2

(12) United States Patent
Gregg

(10) Patent No.: US 12,285,413 B2
(45) Date of Patent: *Apr. 29, 2025

(54) ANTI-VIRAL AGENTS AND METHODS FOR ADMINISTRATION THEREOF

(71) Applicant: John M.H. Gregg, Princeton, NJ (US)

(72) Inventor: John M.H. Gregg, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,508

(22) Filed: Oct. 25, 2022

(65) Prior Publication Data

US 2023/0201167 A1  Jun. 29, 2023

Related U.S. Application Data

(63) Continuation of application No. 17/905,601, filed as application No. PCT/US2021/070300 on Mar. 23, 2021.

(60) Provisional application No. 62/993,121, filed on Mar. 23, 2020.

(51) Int. Cl.
| | | |
|---|---|---|
| *A61K 31/422* | (2006.01) | |
| *A61K 9/00* | (2006.01) | |
| *A61K 31/352* | (2006.01) | |
| *A61K 31/427* | (2006.01) | |
| *A61K 31/496* | (2006.01) | |
| *A61K 31/513* | (2006.01) | |
| *A61K 31/573* | (2006.01) | |
| *A61K 31/675* | (2006.01) | |

(52) U.S. Cl.
CPC ............ *A61K 31/422* (2013.01); *A61K 9/007* (2013.01); *A61K 31/352* (2013.01); *A61K 31/427* (2013.01); *A61K 31/496* (2013.01); *A61K 31/513* (2013.01); *A61K 31/573* (2013.01); *A61K 31/675* (2013.01)

(58) Field of Classification Search
CPC .. A61K 31/422; A61K 31/573; A61K 31/675; A61K 31/427
See application file for complete search history.

(56) References Cited

U.S. PATENT DOCUMENTS

| | | | |
|---|---|---|---|
| 6,531,452 B1 * | 3/2003 | Dragovich | A61P 31/12 514/351 |
| 2023/0263778 A1 * | 8/2023 | Gregg | A61K 9/007 514/365 |

FOREIGN PATENT DOCUMENTS

| | | | | |
|---|---|---|---|---|
| WO | WO-2005113580 A1 * | 12/2005 | | A61K 38/21 |
| WO | WO-2015051268 A2 * | 4/2015 | | A61K 31/427 |
| WO | WO-2021176369 A1 * | 9/2021 | | A61K 31/4025 |

OTHER PUBLICATIONS

Kim et al. Journal of Virology, vol. 86, No. 21, pp. 11754-11762, Nov. 2012. (Year: 2012).*
Nicastri et al. Infect Dis Rep, Feb. 25, 2020, 12(1), 8543. (Year: 2020).*

* cited by examiner

*Primary Examiner* — Kara R. McMillian
(74) *Attorney, Agent, or Firm* — Slavitt IP Law, LLC; Joshua R. Slavitt

(57) ABSTRACT

This invention relates to the use of anti-viral drugs with different mechanisms of action for the treating or preventing of viral infections such as COVID-19 (also known as SARS-CoV-2) and reducing medical complications related to COVID-19 viral disease. The present invention also relates to compositions and combinations of new antiviral drugs, and the administration of these compounds used in these various new combinations, that are incorporated into oral, pulmonary, or intravenous delivery systems.

20 Claims, No Drawings

ANTI-VIRAL AGENTS AND METHODS FOR ADMINISTRATION THEREOF

FIELD OF THE INVENTION

The present invention relates to the use of anti-viral drugs used with different mechanisms of action for the treating or preventing of COVID-19 (also known as SARS-CoV-2) viral infections and reducing medical complications related to COVID-19 viral disease. The present invention also relates to compositions of new chemical entity antiviral drugs and repurposing of existing drugs with antiviral activity into new compositions and combinations, including the introduction of these compounds, used in these various new combinations that are incorporated into a new pulmonary, and a new oral, delivery systems.

The anti-COVID-19 compounds of the present invention may comprise a backbone that includes a drug compound with a particular antiviral mechanism of action, combined with other specific antiviral drugs with different mechanisms of action. The backbones comprise a mechanism that includes, but is not limited to, five major classes of antiviral drugs: 1) phosphatidylserine (PS) modulators that are cortisol and androgen receptor modulators (GCRM/ARMs); 2) Entry Inhibitors (EIs) that are Angiotensin Converting Enzyme-2 (ACE-2) Receptor Blockers that work as ACE-2 attachment entry inhibitors (AEIs) and/or fusion inhibitors (FIs); 3) Protease Inhibitors (PIs); 4) RNA-dependent RNA polymerase inhibitors (RdRpIs) some of which are endosome acidifiers (EAs) that interfere with the replicase and replicase complex including NTPase/RNA-helicases; and 5) MicroRNA Inhibitors (MRIs).

BACKGROUND

Rapid advances in technology of all kinds and advances in travel and globalization have had substantial impacts on improving the human condition within the United States and internationally. These advances, however, have proven to be a double-edged sword, allowing for the easy spread of invasive pathogens causing disease, whether it be accidental or intentional. The United States government has been proactive in its work to legislate and fund medical countermeasures work in response to the potential for public health emergencies initiated by the introduction of pathogens. Key among these responses have been the 2004 Project Bioshield Act and the 2006 Pandemic and All Hazards Preparedness Act, the latter of which provides opportunities through the Biomedical Advanced Research and Development Authority (BARDA).

The National Institute of Allergy and Infectious Diseases Institutes of Health (NIAID), a component of the National Institute of Health (NIH), maintains a list of emerging infectious diseases and pathogens for purposes of prioritization and research guidance. Pathogens are prioritized from A-C based on the traits of transmissibility, morbidity, mortality, and diagnostics With the global pandemic of COVID-19, which first arose in the city of Wuhan in the Hubei province of the Peoples' Republic of China (PRC) and then spread around the world, COVID-19 was placed on this list with medical countermeasures (MCMs) receiving the highest level of priority. The prioritization of MCMs was used as a springboard for study of a series of re-purposed compounds with five different mechanisms of action that have been demonstrated to have COVID-19 antiviral activity and thus have potential as MCMs.

In the evolution of antiviral therapy for human immunodeficiency virus (HIV), drug therapy now consists almost entirely of drugs and drug regimens containing multiple mechanisms of action to control the initiation and process of HIV viral replication. It was found through experience that a single mechanism was often not sufficiently effective as monotherapy and that the HIV virus would develop resistance rapidly. In the same way, multi-mechanism therapy of the COVID-19 virus will be more efficacious with drugs having different mechanisms co-administered as mixtures or fixed dose combinations. The present invention identifies these combination therapies, their method of use and treatment, and novel modes of administration and delivery tailored specifically for the treatment of COVID-19. The present invention also includes a novel pulmonary and oral delivery system for new chemical entity combinations of fixed dose combinations of anti-COVID-19 drugs which dissociate after administration into their original components, as metabolites, that enables more efficient administration and, in the case of pulmonary delivery, delivery more directly to the site of infection in the lungs.

The following sections will provide detailed information on the compounds with the five major classes of antiviral drug mechanisms of Steroid Glucocorticoid Receptor and Androgen Receptor Modulators, EIs, PIs, RdRpIs, and MRIs as exemplified by the compounds Dexamethasone, Valsartan, Rupintrivir, Remdesivir and its Ribose Alcohol Active Metabolite GS-441524, and Hydroxychloroquine, and explains why their activity levels as antivirals against RNA viruses prioritizes their clinical testing for use in mitigation of the duration of COVID-19 infection, severity of COVID-19 infection, and reduction of mortality associated through COVID-19 infection and the reduction of incidence of pneumonia caused by COVID-19 infection.

Dexamethasone is a re-purposed marketed drug that has been placed into a human clinical trial population for COVID-19 as a single agent. Dexamethasone is a potent synthetic member of the glucocorticoid class of steroid drugs with pleiotropic effects on multiple signaling pathways. The biological target is the glucocorticoid receptor. Anti-inflammatory and immunosuppressive effects of dexamethasone are approximately 30 times more potent than cortisol. Anti-inflammatory effects are complex, but primarily via inhibition of inflammatory cells and suppression of expression of inflammatory mediators. To exert an effect, the steroid molecule diffuses across cell membranes and binds to glucocorticoid receptors, which causes a conformational change in the receptor. The receptor-glucocorticoid complex is able to move into the cell nucleus, where it dimerizes and binds to glucocorticoid response elements.

The anti-inflammatory effects of dexamethasone are complex, but primarily via inhibition of inflammatory cells and suppression of expression of inflammatory mediators. Use is for treatment of inflammatory and immune-mediated disease formulated for intravenous and oral administration. In the present invention, the dexamethasone drug product will be delivered directly to the respiratory tract, including nasal, throat, and lung tissue, via inhalation from a vape pen or electronic cigarette/portable medical vaporizer in either a free base gas form or ultrafine particles and in combination during inhalation with antivirals like Remdesivir or Remdesivir's Ribose Alcohol Active Metabolite GS-441524. Like most steroid compounds, Dexamethasone is a cortisol/glucocorticoid and androgen modulator (GCRM/ARMs).

Dexamethasone has at least three general mechanisms of anti-viral action effect against COVID-19. The first antiviral effects are mediated through binding of its molecules to glucocorticoid response elements (GREs) present in some viral genomes. The second is through binding of these molecules to phosphatidylserine (PS) present in the envelope of all enveloped viruses, and the third is through signaling effects in the immune system that modulate appropriate responses to the viral pathogens that facilitate immune response without an exaggerated effect that damages tissue.

The mechanism of action through binding to GRE's is as follows: Viruses that infect animals and humans infect cells by placing their genetic material within the cytoplasm and/or nucleoplasm of the infected cell. "Response elements" within the genome, which may comprise coding regions or non-coding regions, respond to molecular signaling of the host cell and/or other elements of the virus' own molecular network. Viruses often have GREs, namely response elements that are under the influence of glucocorticoid signaling mediated by the binding of cortisol (or other glucocorticoids) to the glucocorticoid receptor (GCR).

Viruses that have been identified as having GREs include: COVID-19, MERS, SARS, Herpes Virus-7 (HHV-7), Kaposi's Sarcoma-Associated Herpes virus (or Human Herpes Virus-8 [HHV-8], Variola (Small Pox) virus, Vaccinia virus, Cowpox virus, and Monkey-pox virus.

Binding of Dexamethasone, as GCR and androgen receptor (AR) modulators, also modulate the viral GRE to directly or indirectly inhibit fundamental viral functions (including, but not limited to genetic replication, production of virus-associated proteins, assembly of genetic material and viral proteins into complete viruses, increasing genetic diversity, promotion of viral active or passive virus release from the cell, and viral infectivity.

The mechanisms of anti-viral action related to PS binding are as follows: PS is normally sequestered to the inner leaflet of the plasma membrane bilayer, but during apoptosis the mechanism that normally maintains PS in the inner leaflet is down-regulated, allowing the appearance of PS on the cell surface. PS exposure is a recognition signal for phagocytic cells that clear dying cells. Several macrophage receptors have been implicated in recognizing PS on apoptotic cells, including various scavenger receptors, CD36, CD14, and PS receptor (PSR). Thus, PS has a demonstrated ability to mediate cell-cell interactions and to function as a ligand for a variety of PS-binding receptors.

Enveloped viruses expose PS on their host-captured lipid bilayer membranes constantly. Enveloped viruses utilize this PS-exposure to evade attacks by the human immune system and to enter phagocytic cells like monocytes/macrophages making its appearance in the viral membrane highly suspect as a factor in virus-target cell fusion.

Valsartan, as an antiviral entry inhibitor (EI), is a re-purposed marketed drug that could be rapidly placed into a human clinical trial population for COVID-19 Valsartan, a compound that has been approved as an antihypertensive, is in the class of angiotensin receptor blocker (ARB) drugs. ARBs block the angiotensin-2 converting enzyme (ACE-2) receptor that is physiologically involved in the regulation of blood pressure, among other functions. This ACE-2 receptor is also the ligand expressed on the surface of human lung cells to which the COVID-19 virus spike protein (SP) binds to initiate the process of cellular infection, including attachment, membrane integration, and viral RNA insertion. By blocking access to the ACE-2 receptor expressed on human lung cells, Valsartan, or other ARBs, work as both attachment entry inhibitors (AEIs) and/or fusion inhibitors (FIs) that inhibit the binding of the COVID-19 spike protein from binding to the lung epithelial cells which results in SP conformational change to allow membrane fusion and viral RNA insertion.

Oral administration of Valsartan, as an exemplar of ARBs, would be limited in its utility, in the case of its use for the treatment for COVID-19, because of its systemic effect on blood pressure, which would be dose related.

Rupintrivir, as an antiviral protease inhibitor (PI), is a re-purposed clinical stage drug that could be rapidly placed into a human clinical trial population for COVID-19. Rupintrivir, a compound that was originally developed by Pfizer as an antiviral drug for the common cold caused by picornavirus infection, is in the class of 3C protease drugs designed to block the protease that cleaves the polyprotein of RNA viruses. While there are differences in the RNA genetic sequences of the cleavage sites targeted by picornavirus proteases to those by coronavirus protease cleavage sites for COVID-19, the proteases are sufficiently similar that the activity inhibited is "3C Like" (3CL) and can be blocked or inhibited in the same manner, and even more efficiently in a combination with other related protease inhibitors, like the HIV protease inhibitors, as exemplified by Ritonovir, possibly due to enhanced stearic hindrance, or the Hepatitis C proteases that have inhibitory effects on the other proteases involved with COVID-19 infections, including the cathepsin L-dependent viral glycoprotein involved in the activation via SARS-CoV S-protein cleavage at S1/S2 boundary under low pH conditions, and involvement of transmembrane protease serine 2 (TMPRSS2), which is active in triggering the cleavage of trimer S-protein (Simmons et al., 2005; Millet and Whittaker, 2015).

Ritonovir, as an antiviral protease inhibitor (PI), is a re-purposed marketed anti-HIV drug that could be rapidly placed into a human clinical trial population for COVID-19. Ritonovir, and other HIV PIs, like atazanovir, are compounds that were originally developed as antiviral drugs in the class of HIV protease drugs designed to block proteases that cleave polyproteins. The proteases for HIV and coronaviruses are sufficiently functionally similar that the activity inhibited is "3C Like" (3CL) and can be blocked or inhibited in the same manner, and even more efficiently in a combination with other related protease inhibitors, like the picornavirus PI, Rupintrivir, possibly due to enhanced stearic hindrance.

Myricetin is a re-purposed marketed supplement that could be rapidly placed into a human clinical trial population for COVID-19. Myricetin is an RNA-dependent RNA polymerase inhibitor (RdRpI) that interferes with the COVID-19 replicase/replicase complex. Specifically, it inhibits NTPase/RNA-helicases (that unwind highly base-paired regions of the RNA genome and supply energy for the polymerization process). Myricetin is a common plant-derived flavonoid and is well recognized for its nutraceutical value. It is one of the key ingredients of various foods and beverages. Myricetin also impacts the biochemical efficacy and binding ability of large intracellular biomolecules. Myricetin has been shown to inhibit cellular RNA polymerase. Myricetin (CID 5281672) also inhibits closely related SARS-CoV helicase with an IC50 value of 2.7 µM and acceptable selectivity index.

Rifampin, a re-purposed marketed drug that could be rapidly placed into a human clinical trial population for COVID-19. Rifampin is an RNA-dependent RNA polymerase inhibitor (RdRpI) that interferes with the COVID-19 replicase/replicase complex. Like Myricetin, it inhibits NTPase/RNA-helicases (that unwind highly base-paired regions of the RNA genome and supply energy for the polymerization process). Rifampin, also known as rifampicin, is the prototypical antibiotic in its class used to treat several types of bacterial infections. Crystal structure data and biochemical data suggest that rifampicin binds to the pocket of the RNA polymerase β subunit. The Rifampin drug, acting as an inhibitor, prevents RNA synthesis by physically blocking elongation, and thus preventing synthesis of host bacterial proteins. By this "steric-occlusion" mechanism, rifampicin blocks synthesis of the second or third phosphodiester bond between the nucleotides in the RNA backbone, preventing elongation of the 5' end of the RNA transcript past more than 2 or 3 nucleotides. Rifampin thus binds to RNA polymerase at a site adjacent to the RNA polymerase active center and blocks RNA synthesis by physically blocking the formation of the phosphodiester bond in the RNA backbone, preventing extension of RNA products beyond a length of 2-3 nucleotides. Therefore, Rifampin has been shown to inhibit cellular RNA polymerase.

Remdesivir (GS-5734) is a re-purposed clinical stage anti-Ebola RdRpIs drug that could be rapidly placed into a human clinical trial population for COVID-19 in inhaled delivery systems as well as a combination therapy with other antivirals Remdesivir was reported to inhibit SARS-CoV and MERS-CoV replication in multiple in vitro systems, including primary human airway epithelial cell cultures with submicromolar EC50 values (Sheahan et al., 2017). Experimental evaluation of GS-5734 in a mouse model of SARS-CoV infection showed that its prophylactic and early therapeutic administration reduced lung viral load and improved respiratory function along with other clinical signs. Similarly, it has shown antiviral activity in SARS-CoV-2 in-vitro models and was evaluated in the U.S. and other countries in clinical trials for COVID-19 and has been cleared for the use in the U.S. by FDA, first with an emergency use authorization (EUA) and then through a New Drug Application (NDA) in an intravenous formulation for moderate to severe COVID-19 patients in a hospital setting.

Hydroxychloroquine is a re-purposed marketed drug that could be rapidly placed into a human clinical trial population for COVID-19 in a respiratory format delivered by an electronic cigarette or vape pen to maximize local concentrations to nasal, throat, and lung tissue while minimizing systemic concentrations that could result in significant concentrations accumulating in cardiac tissue that might adversely affect heart rhythm. Hydroxychloroquine is a microRNA inhibitor (MRI) and endosome acidifier (EA) that is an aminoquinoline class antimalarial drug that was developed as a derivative of the drug quinine. Hydroxychloroquine has been shown in in-vitro systems to have inhibitory effects of coronavirus replication and there has been anecdotal evidence of clinical benefit in in-vivo human usage. A microRNA (miRNA) is a small non-coding RNA molecule (containing about 22 nucleotides) found in plants, animals, and some viruses, including SARS-CoV-2 that functions in RNA silencing and post-transcriptional regulation of gene expression. It has been found that miRNAs function via base-pairing with complementary sequences within mRNA molecules. As a result, these mRNA molecules are silenced, by one or more of the following processes: (1) Cleavage of the mRNA strand into two pieces, (2) Destabilization of the mRNA through shortening of its poly(A) tail, and (3) Less efficient translation of the mRNA into proteins by ribosomes. miRNAs resemble the small interfering RNAs (siRNAs) of the RNA interference (RNAi) pathway, except miRNAs derive from regions of RNA transcripts that fold back on themselves to form short hairpins, whereas siRNAs derive from longer regions of double-stranded RNA. The human genome may encode over 1900 miRNAs. MRIs, such as quinine lack alkaloids, such as hydroxychloroquine, and interfere with the formation and metabolic activity of miRNAs that are integral to viral replication processes of COVID-19.

BRIEF SUMMARY OF THE INVENTION

The present invention relates to the use of PS GR/AR modulators or active agents (e.g., Dexamethasone), optionally in combination with at least one other agent, for treating or preventing COVID-19 infection disease and its complications.

The present invention also relates to the pulmonary administration of Valsartan, and includes but is not limited to, the other drugs in the ARB class, in this respiratory mode of administration, which encompasses, but is not limited to, inhalers, nebulizers, and electronic/vaping cigarettes.

The present invention also relates to the use of ARBs as EIs (e.g., Valsartan), optionally in combination with at least one other agent with a different COVID-19 antiviral mechanism, for treating or preventing COVID-19 infection disease and its complications. These ARBs can be delivered in both oral and respiratory formats.

The present invention also relates to the use of Rupintrivir as a PI, optionally in combination with a complimentary PI, including an HIV PI, like Ritonovir, and at least one other agent with a different COVID-19 antiviral mechanisms, for treating or preventing COVID-19 infection disease and its complications. These PIs can be delivered in both oral and respiratory formats.

The present invention also relates to the use of a picornavirus 3C or 3C like (3CL) PI, such as Rupintrivir, and at least one other agent with a different COVID-19 antiviral mechanism, for treating or preventing COVID-19 infection disease and its complications including PIs and drugs with activity against cathepsin L-dependent viral glycoprotein and or transmembrane protease serine 2 (TMPRSS2). These PIs can be delivered in both oral and respiratory formats, optionally in combination with one or more of the complimentary anti-viral drugs from the five classes outlined above.

The present invention also relates to the use of flavonoids, exemplified by Myricetin, as an RdRpI that interferes with the replicase complex, optionally in combination with another RdRpI such as Rifampin, and at least one other agent with a different COVID-19 antiviral mechanisms, for treating or preventing COVID-19 infection disease and its complications. These RdRpIs can be delivered in both oral and respiratory formats.

The present invention also relates to the use of Rifampicin-class antibiotics, exemplified by Rifampin, as RdRpIs that interfere with the replicase complex, optionally in combination with another RdRpI such as Myricetin, and at least one other agent with a different COVID-19 antiviral mechanisms, for treating or preventing COVID-19 infection disease and its complications. These RdRpIs can be delivered in both oral and respiratory formats.

The present invention also relates to the use of Remdesivir and its active ribose alcohol metabolite as an RdRpIs that interferes with the replicase complex, optionally in combination with one or more RdRpIs such as Myricetin and or Rifampin, and at least one other agent with a different COVID-19 antiviral mechanisms, such as Dexamethasone or Hydroxychloroquine (in its racemic mixture or purified enantiomers), for treating or preventing COVID-19 infection disease and its complications. These RdRpIs can be delivered in both oral and respiratory formats.

The present invention also relates to the use of hydroxychloroquine and related aminoquinolines and aryl-amino alcohols as MRIs and EAs that interfere with the miRNA formation that inhibits viral replication, optionally in combination at least one other agent with a different COVID-19 antiviral mechanism, for treating or preventing COVID-19 infection disease and its complications. These MRIs can be delivered in both oral and respiratory formats.

In one embodiment, the present invention includes a pulmonary delivery system that comprises two, three, or more drugs that are joined through a chemical linkage or linker that is covalently linked at one end to one drug compound on a suitable attachment chemical group and covalently linked at the other end to another drug compound, also on a suitable attachment group, thus forming a new chemical entity (NCE) drug conjugate that can be then pyrolytically decoupled by heat in a medical vaporizer, including portable medical vaporizers like electronic cigarettes and vape pens, to present to patients inhaled drugs that are combinations of compounds characterized in other settings that are introduced to the patient in a gas or ultrafine particle aerosol form. In one embodiment, the NCE at an appropriate therapeutic dosage level is loaded into a cartridge of an electronic cigarette with replaceable cartridges, or a single use electronic cigarette. When the electronic cigarette, having a temperature setting feature, is activated, the heat generated in the electronic cigarette, 380-480 degrees Fahrenheit, is sufficient to break the bonds on the chemical linkage or linker to the attached therapeutic compounds so that the inhaled drug vapor gas aerosol or aerosol of ultrafine particles contains the therapeutic drugs that are released for inhalation to the human or animal patient. The chemical linkage between antiviral agents may comprise one or more carbonate or carbamate groups.

In one embodiment, the present invention includes the pulmonary delivery of drugs with one or more Entry Inhibitors (EIs) paired with one or more RNA-dependent RNA polymerase inhibitors (RdRpIs) including, but not limited to, a combination of Valsartan+Rifampin, a combination of Valsartan+Myricetin, and a combination of Valsartan+Remdesivir or Valsartan+Remdesivir's Ribose Alcohol Active Metabolite GS-441524. The Valsartan/Rifampin combination may be administered by a nebulizer device with therapeutically appropriate doses loaded in powder or paste form or by vapor through an electronic cigarette where the Valsartan and Rifampin compounds are covalently linked through a chemical linker to form a new chemical entity compound, BB-700, with the base compounds, Valsartan and Rifampin, forming the two major functional components that dissociate into metabolites comprising Valsartan and Rifampin base compounds through heat providing the vaporization in the electronic cigarette, such that the compounds delivered in a vapor format to lung cells will be the Valsartan and Rifampin components. Alternatively, Valsartan+Myricetin may be administered by a nebulizer device with therapeutically appropriate doses loaded in powder or paste form or by vapor through an electronic cigarette where the Valsartan and Myricetin compounds are covalently linked through a chemical linker to form a new chemical entity compound, BB-701, with the base compounds, Valsartan and Rifampin, forming the two major functional components that dissociate into metabolites comprising Valsartan and Rifampin base compounds through heat providing the vaporization in the electronic cigarette, such that the compounds delivered in a vapor format to lung cells will be the Valsartan and Myricetin components. In another embodiment, Valsartan and Remdesivir can be administered by a nebulizer device with therapeutically appropriate doses loaded in powder or paste form or by vapor through an electronic cigarette where the Valsartan and Remdesivir compounds are covalently linked through a chemical linkage or linker to form a new chemical entity compound, BB-702, or BB-702B for Valsartan and the Ribose Alcohol Active Metabolite GS-441524 of Remdesivir, with the base compounds, Valsartan and Remdesivir (or its ribose alcohol active metabolite), forming the two major functional components that dissociate into metabolites comprising Valsartan and Remdesivir (or its ribose alcohol active metabolite) base compounds through heat providing the vaporization in the electronic cigarette, such that the compounds delivered in a vapor format to lung cells will be the Valsartan and Remdesivir (or its ribose alcohol active metabolite) components.

In one embodiment, the present invention includes the pulmonary delivery of drugs with one or more Entry Inhibitors (EIs) paired with one or more protease inhibitors including, but not limited to, a combination of Valsartan+Rupintrivir. The Valsartan and Rupintrivir combination may be administered by a nebulizer device with therapeutically appropriate doses loaded in powder or paste form or by vapor through an electronic cigarette where the Valsartan and Rupintrivir compounds are covalently linked through a chemical linker to form a new chemical entity compound, BB-703, with the base compounds, Valsartan and Rupintrivir, forming the two major functional components that dissociate into metabolites comprising Valsartan and Rupintrivir base compounds through heat providing the vaporization in the electronic cigarette, such that the compounds delivered in a vapor format to lung cells will be the Valsartan and Rupintrivir components.

In one embodiment, the present invention includes the pulmonary delivery of drugs with one or more Entry Inhibitors (EIs) paired with one or more MRIs including, but not limited to, a combination of Valsartan+Hydroxychloroquine. The Valsartan and Hydroxychloroquine combination can be administered by a nebulizer device with therapeutically appropriate doses loaded in powder or paste form or by vapor through an electronic cigarette where the Valsartan and Hydroxychloroquine compounds are covalently linked through a chemical linker to form a new chemical entity compound, BB-704, with the base compounds, Valsartan and Hydroxychloroquine, forming the two major functional components that dissociate into metabolites consisting of the Valsartan and Hydroxychloroquine base compounds through heat providing the vaporization in the electronic cigarette, such that the compounds delivered in a vapor format to lung cells will be the Valsartan and Hydroxychloroquine components.

In one embodiment, the present invention includes the pulmonary delivery of one or more RdRpIs including, but not limited to, a combination of Rifampin and Myricetin. The Rifampin and Myricetin combination can be administered by a nebulizer device with therapeutically appropriate doses loaded in powder or paste form or by vapor through an electronic cigarette where the Rifampin and Myricetin compounds are covalently linked through a chemical linker to form a new chemical entity compound, BB-705, with the base compounds, Rifampin and Myricetin, forming the two major functional components that dissociate into metabolites consisting of the Rifampin and Myricetin base compounds through heat providing the vaporization in the electronic cigarette, such that the compounds delivered in a vapor format to lung cells will be the original Rifampin and Myricetin components.

In one embodiment, the present invention includes the pulmonary delivery of one or more RNA-dependent RNA polymerase inhibitors (RdRpIs) and one or more MRIs, including but not limited to, a combination of Rifampin+Hydroxychloroquine, a combination of Myricetin+Hydroxychloroquine, or a combination of Remdesivir+Hydroxychloroquine or a combination of Remdesivir's Ribose Alcohol Active Metabolite GS-441524+Hydroxychloroquine. The Rifampin and Hydroxychloroquine combination can be administered by a nebulizer device with therapeutically appropriate doses loaded in powder or paste form or by vapor through an electronic cigarette where the Rifampin and Hydroxychloroquine compounds are covalently linked through a chemical linker to form a new chemical entity compound, BB-706, with the base compounds, Rifampin and Hydroxychloroquine, forming the two major functional components that dissociate into metabolites consisting of the Rifampin and Hydroxychloroquine base compounds through heat providing the vaporization in the electronic cigarette, such that the compounds delivered in a vapor format to lung cells will be the Rifampin and Hydroxychloroquine components. Alternatively, Myricetin+Hydroxychloroquine can be administered by a nebulizer device with therapeutically appropriate doses loaded in powder or paste form or by vapor through an electronic cigarette where the Myricetin and Hydroxychloroquine compounds are covalently linked through a chemical linker to form a new chemical entity compound, BB-707, with the base compounds, Myricetin and Hydroxychloroquine, forming the two major functional components that will dissociate into metabolites consisting of the Myricetin and Hydroxychloroquine base compounds through heat providing the vaporization in the electronic cigarette, such that the compounds delivered in a vapor format to lung cells will be the Myricetin and Hydroxychloroquine components. In another embodiment, Remdesivir, or Remdesivir's Ribose Alcohol Active Metabolite GS-441524, and Hydroxychloroquine can be administered by a nebulizer device with therapeutically appropriate doses loaded in powder or paste form, or by electronic cigarette (vape pen or medical vaporizer) vapor in a gas or ultrafine particle aerosol through an electronic cigarette where the Remdesivir (or its Ribose Alcohol Active Metabolite GS-441524) and Hydroxychloroquine compounds are covalently linked through a chemical linkage or linker to form a new chemical entity compound, BB-708 (or BB-708B in the case of the combination with the Remdesivir Ribose Alcohol Active Metabolite GS-441524), with the base compounds, Remdesivir (or its Ribose Alcohol Active Metabolite GS-441524) and Hydroxychloroquine (either in its racemic mixture or purified R or S enantiomers), forming the two major functional components that dissociate into metabolites consisting of the Remdesivir (or its Ribose Alcohol Active Metabolite GS-441524) and Hydroxychloroquine base compounds through heat providing the vaporization in the electronic cigarette, such that the compounds delivered in a vapor format to lung cells will be the Remdesivir (or its Ribose Alcohol Active Metabolite GS-441524) and Hydroxychloroquine components.

In one embodiment, the present invention includes the pulmonary delivery of one or more RNA-dependent RNA polymerase inhibitors (RdRpI) and one or more PIs including, but not limited to, a combination of Rifampin+Ritonavir. The Rifampin and Ritonavir combination can be administered by a nebulizer device with therapeutically appropriate doses loaded in powder or paste form or by vapor through an electronic cigarette where the Rifampin and Ritonavir compounds are covalently linked through a chemical linker to form a new chemical entity compound, BB-709, with the base compounds, Rifampin and Ritonavir, forming the two major functional components that dissociate into metabolites consisting of the Rifampin and Ritonavir base compounds through heat providing the vaporization in the electronic cigarette, such that the compounds delivered in a vapor format to lung cells will be the Rifampin and Ritonavir components.

In one embodiment, the present invention includes the pulmonary delivery of one or more RNA-dependent RNA polymerase inhibitors (RdRpI) and one or more glucocorticoid steroids or glucocorticoid receptor or androgen receptor modulators including, but not limited to, a combination of Remdesivir (or Remdesivir's Ribose Alcohol Active Metabolite GS-441524)+Dexamethasone. The Remdesivir (or Remdesivir's Ribose Alcohol Active Metabolite GS-441524) and Dexamethasone combination can be administered by a nebulizer device with therapeutically appropriate doses loaded in powder or paste form, or by vapor through an electronic cigarette where the Remdesivir (or Remdesivir's Ribose Alcohol Active Metabolite GS-441524) and Dexamethasone compounds are covalently linked through a chemical linkage or linker to form a new chemical entity compound, BB-710 (for the compound containing Remdesivir) and BB-710B (for the compound containing Remdesivir's Ribose Alcohol Active Metabolite GS-441524), with the base compounds, Remdesivir (or Remdesivir's Ribose Alcohol Active Metabolite GS-441524) and Dexamethasone, forming the two major functional components that dissociate into metabolites consisting of the Remdesivir (or Remdesivir's Ribose Alcohol Active Metabolite GS-441524) and Dexamethasone base compounds through heat provided by the vaporization in the electronic cigarette or medical vaporizer, such that the compounds delivered in a vapor format to lung cells as a gas or ultrafine particles in an aerosol will be the Remdesivir (or Remdesivir's Ribose Alcohol Active Metabolite GS-441524) and Dexamethasone components.

In one embodiment, the present invention includes the pulmonary delivery of one or more PIs and one or more MRIs including, but not limited to, a combination Rupintrivir+Hydroxychloroquine. This combination can be administered by a nebulizer device with therapeutically appropriate doses loaded in powder or paste form or by vapor through an electronic cigarette where the Rupintrivir and Hydroxychloroquine compounds are covalently linked through a chemical linker to form a new chemical entity compound, BB-711, with the base compounds, Rupintrivir and Hydroxychloroquine, forming the two major functional components that dissociate into metabolites consisting of the Rupintrivir and Hydroxychloroquine base compounds through heat providing the vaporization in the electronic cigarette, such that the compounds delivered in a vapor format to lung cells will be the Rupintrivir and Hydroxychloroquine components.

In one embodiment, the present invention includes the oral delivery of one or more glucocorticoid steroids or glucocorticoid receptor or androgen receptor modulators (GRSM/ARMs) and one or more RNA-dependent RNA polymerase inhibitors (RdRpIs) including, but not limited to, a combination of mifepristone+rifampin. This combination can be administered as an oral solid or oral liquid suspension dosing form or by a fixed dose oral solid or oral liquid suspension dosing form where the Mifepristone and Rifampin compounds in the fixed dose dosage form are covalently linked through a chemical linker to form a new chemical entity compound, BB-712, with the base compounds, Mifepristone and Rifampin, forming the two major functional components that dissociate into metabolites consisting of the Mifepristone and Rifampin base compounds through the pH of the stomach with acidity sufficient to separate the base compounds from the linker to yield in the stomach for gastric absorption the Mifepristone and Rifampin components.

In one embodiment, the present invention includes the oral delivery of one or more PSIs and at least two PIs including, but not limited to, a combination of Relacorilant+Rupintrivir+Ritonavir. This combination can be administered in an oral solid or oral liquid suspension dosing form or by a fixed dose oral solid or oral liquid suspension dosage form where the Relacorilant and Rupintrivir and Ritonavir compounds in the fixed dose dosage form are covalently linked through a chemical linker to form a new chemical entity compound, BB-713, with the base compounds, Relacorilant and Rupintrivir and Ritonavir, forming the three major functional components that dissociate into metabolites consisting of the Relacorilant and Rupintrivir and Ritonavir base compounds through the pH of the stomach with acidity sufficient to separate the base compounds from the linker to yield in the stomach for gastric absorption the Relacorilant and Rupintrivir and Ritonavir components.

In one embodiment, the present invention includes the oral delivery of one or more PSIs and one or more MRIs including, but not limited to, a combination of Miricorilant+Hydroxychloroquine. This combination can be administered in an oral solid or oral liquid suspension dosing form or by a fixed dose oral solid or oral liquid suspension dosage form where the Miricorilant and Hydroxychloroquine compounds in the fixed dose dosage form are covalently linked through a chemical linker to form a new chemical entity compound, BB-714, with the base compounds, Miricorilant and Hydroxychloroquine, forming the two major functional components that dissociate into metabolites consisting of the Miricorilant and Hydroxychloroquine base compounds through the pH of the stomach with acidity sufficient to separate the base compounds from the linker to yield in the stomach for gastric absorption the Miricorilant and Hydroxychloroquine components.

In one embodiment, the present invention includes the oral delivery of at least two PIs including, but not limited to, a combination of rupintrivir+ritonavir and a combination of rupintrivir+ritonavir+lopinavir. These combinations can be administered in an oral solid or oral liquid suspension dosing form or by a fixed dose oral solid or oral liquid suspension dosage form where the rupintrivir and ritonavir compounds in the fixed dose dosage form are covalently linked through a chemical linker to form a new chemical entity compound, BB-715, with the base compounds, Rupintrivir and Ritonavir, forming the two major functional components that dissociate into metabolites consisting of the Rupintrivir and Ritonavir base compounds through the pH of the stomach with acidity sufficient to separate the base compounds from the linker to yield in the stomach for gastric absorption the Rupintrivir and Ritonavir components. In oral administration of Lopinavir for HIV, the available drug may be boosted with the addition of Ritonavir, which blocks enzymes in the cytochrome P450 system to make human drug dosing of effective antiviral drug levels for HIV possible. Thus, to potentially gain benefits in higher drug exposure for COVID-19, an alternative combination of Rupintrivir+Ritonavir+Lopinavir can be administered in an oral solid or oral liquid suspension dosing form or by a fixed dose oral solid or oral liquid suspension dosage form where the Rupintrivir and Ritonavir and Lopinavir compounds in the fixed dose dosage form are covalently linked through a chemical linker to form a new chemical entity compound, BB-716, with the base compounds, Rupintrivir and Ritonavir and Lopinavir, forming the three major functional components that dissociate into metabolites consisting of the Rupintrivir and Ritonavir and Lopinavir base compounds through the pH of the stomach with acidity sufficient to separate the base compounds from the linker to yield in the stomach for gastric absorption the Rupintrivir and Ritonavir and Lopinavir components.

In one embodiment, the invention provides a compound selected from the group consisting of Glucocorticoids and Glucocorticoid Receptor Modulators and Androgen Receptor Modulators (GCRM/ARMs) that also modulate phosphatidylserine (PS) as exemplified by:

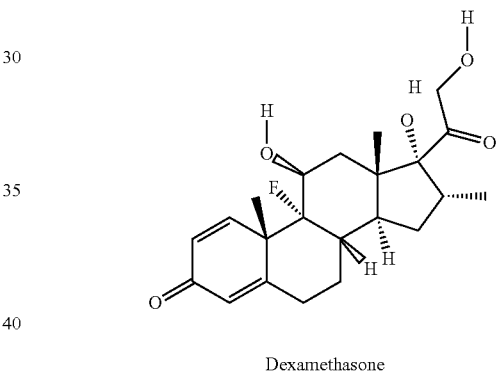

Dexamethasone or a pharmaceutically acceptable salt thereof;

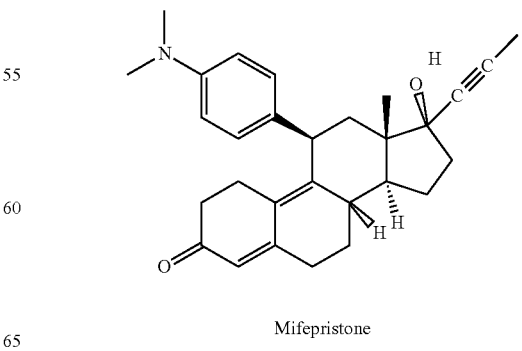

Mifepristone or a pharmaceutically acceptable salt thereof;

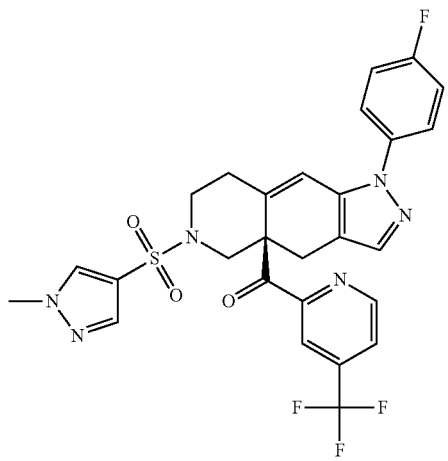

Relacorilant or a pharmaceutically acceptable salt thereof; and

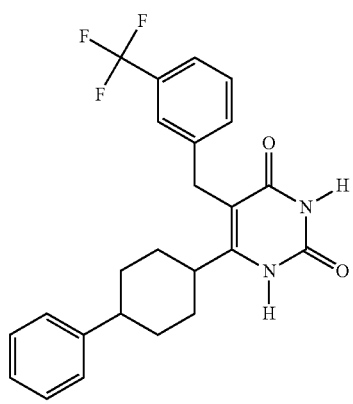

Miricorilant or a pharmaceutically acceptable salt thereof, and combinations thereof.

In one embodiment, the invention provides a pharmaceutical composition comprising a therapeutically effective amount of at least one active agent, wherein the active agent is selected from the group consisting of Entry Inhibitors (EIs) that are Angiotensin Converting Enzyme-2 (ACE-2) Receptor Blockers that work as ACE-2 attachment entry inhibitors (AEIs) or fusion inhibitors (FIs) as exemplified by Angiotensin Receptor Blockers (ARBs) such as:

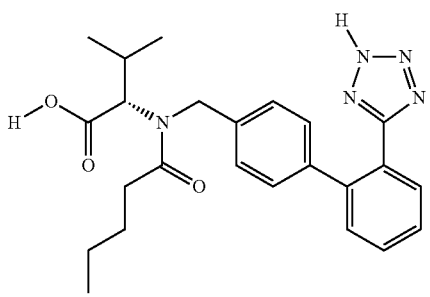

Valsartan or a pharmaceutically acceptable salt thereof.

In one embodiment, the invention provides a pharmaceutical composition comprising a therapeutically effective amount of at least one active agent, wherein the active agent is selected from the group consisting of Protease Inhibitors (PIs) as exemplified by:

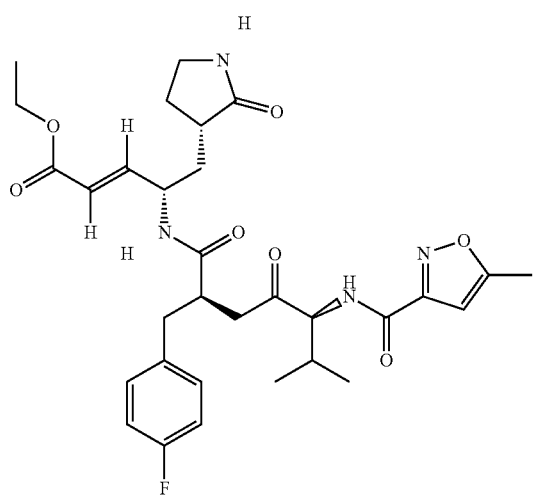

Rupintrivir or a pharmaceutically acceptable salt thereof, and

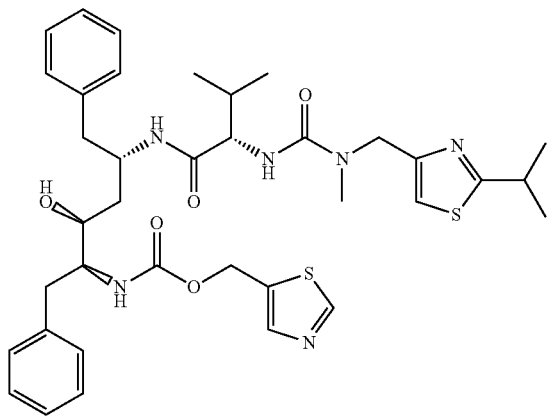

Ritonavir or a pharmaceutically acceptable salt thereof, and combinations thereof.

In one embodiment, the invention provides a pharmaceutical composition comprising a therapeutically effective amount of at least one active agent, wherein the active agent is selected from the group consisting of RNA-dependent RNA polymerase inhibitors (RdRpIs) that interfere with the replicase and replicase complex including NTPase/RNA-helicases as exemplified by:

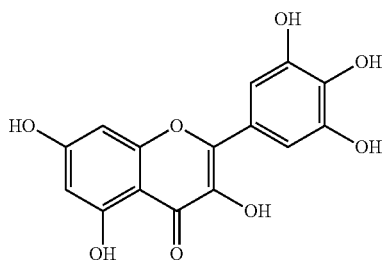

Myricetin or a pharmaceutically acceptable salt thereof,

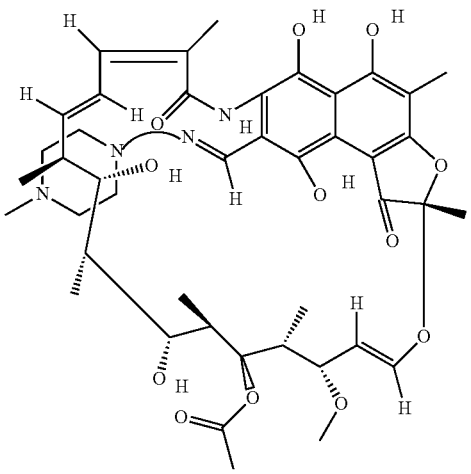

Rifampin or a pharmaceutically acceptable salt thereof,

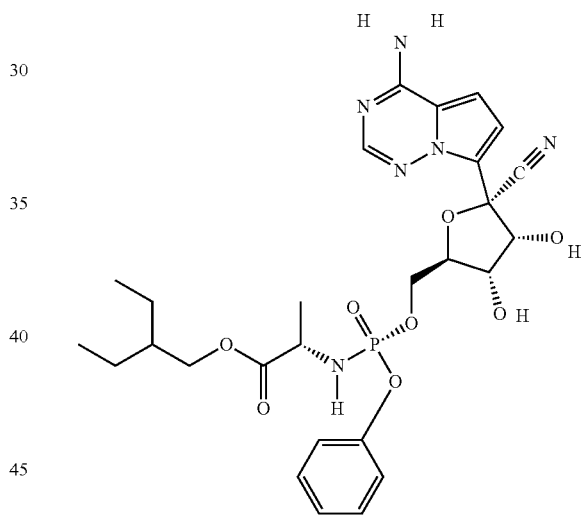

Remdesivir or a pharmaceutically acceptable salt thereof,
the Ribose Alcohol Active Metabolite GS-441524 of Remdesivir:

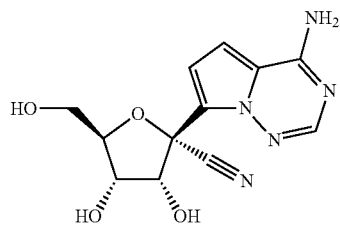 [SMILES: N#C[C@@]1(c2ccc3c(N)ncnn23)O[C@H](CO)[C@@H](O)[C@H]1O]

or a pharmaceutically acceptable salt thereof, and combinations thereof.

In one embodiment, the invention provides a pharmaceutical composition comprising a therapeutically effective amount of at least one active agent, wherein the active agent is selected from the group consisting of MicroRNA Inhibitors (MRIs) and Endosome Acidifiers (EAs) as exemplified by:

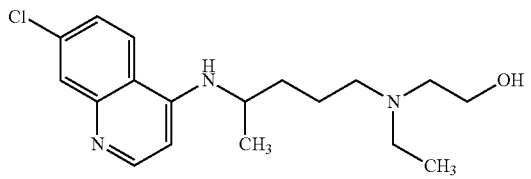

Hydroxychloroquine or a pharmaceutically acceptable salt thereof.

In one embodiment, the invention provides a pharmaceutical composition comprising a therapeutically effective amount of BB-708, also labeled as Plaquemdesivir:

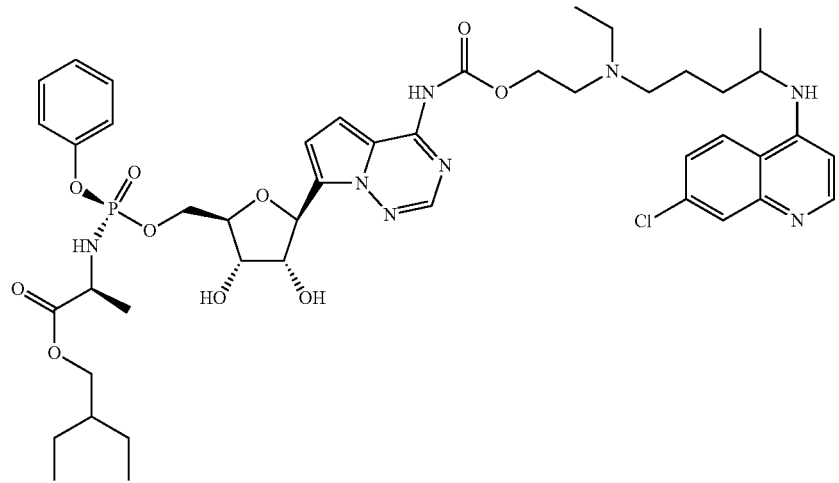

Plaquemdesivir
Chemical Formula: $C_{45}H_{60}ClN_8O_{10}P$
Molecular Weight: 939.44
tPSA: 217.47
CLogP: 4.703 or a pharmaceutically acceptable salt thereof.

In one embodiment, the invention provides a pharmaceutical composition comprising a therapeutically effective amount of BB-708B, also labeled as Riboplaquemdesivir:

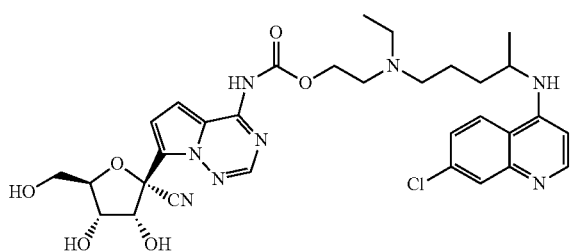

+ carbonate isomer from 5'-ribose alcohol
Chemical Formula: $C_{21}H_{37}ClN_8O_6$
Molecular Weight: 653.14 or a pharmaceutically acceptable salt thereof.

In one embodiment, the invention provides a pharmaceutical composition comprising a therapeutically effective amount of a drug conjugate of the free base of the ribose alcohol active metabolite of Remdesivir and Dexamethasone, linked with a carbamate, to form the new chemical entity, BB-710B, also labeled as Dexadesivir:

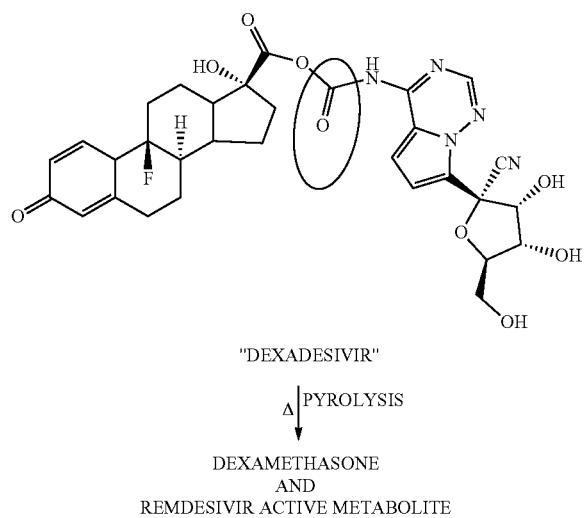

"DEXADESIVIR"

Δ | PYROLYSIS

DEXAMETHASONE
AND
REMDESIVIR ACTIVE METABOLITE or a pharmaceutically acceptable salt thereof.

In one embodiment, the present invention includes the synthesis of BB-708, Plaquemdesivir, in an embodiment using a chemistry that includes the procedure whereby Hydroxychloroquine (100 mg, 1.0 equiv, MW 335.88) is suspended in 2 mL of DCM and 2 mL of DMF and 1.2 equiv. CDI (carbonyl diimidazole) and TEA 5.0 equiv. is added. The reaction is stirred at 45° C. for 2.5 hours. Remdesivir is then added, and the reaction is heated to 55° C. and stirred for 1 hour. The product of this reaction has molecular weight of 964.45.

In one embodiment, the present invention includes the synthesis of BB-708B, Riboplaquemdesivir, in an embodiment using a chemistry that includes the procedure whereby Hydroxychloroquine (100 mg, 1.0 equiv, MW 335.88) is suspended in 2 mL of DCM and 2 mL of DMF and 1.2 equiv. CDI (carbonyl diimidazole) and TEA 5.0 equiv. is added. The reaction is stirred at 45° C. for 2.5 hours. The ribose alcohol active metabolite of Remdesivir (GS-441524) is then added, and the reaction is heated to 55° C. and is stirred for 1 hour. The product of this reaction has molecular weight of 653.14.

In one embodiment, the invention comprises a pharmaceutical composition in a dosage form selected from the group consisting of a minicapsule, capsule, tablet, implant, troche, lozenge, minitablet, temporary or permanent suspension, injectable, ovule, suppository, wafer, chewable tablet quick or fast dissolving tablet, effervescent tablet, buccal or sublingual solid, granule, film, sprinkle, pellet, topical formulation, patch, bead, pill, powder, triturate, smart pill, smart capsule, platelet, strip, and sachet.

In one embodiment, the invention comprises a pharmaceutical composition in a dosage form for respiratory application, and optionally at least one pharmaceutically acceptable excipient, such as Vegetable Glycerin (VG) and/or Propylene Glycol (PG). In such embodiment, the dosage form may be selected from the group consisting of: spray, inhaler, aerosol, vapor, vape cigarette, electronic cigarette with a cartridge to hold drug for vaporizing, single use electronic cigarette, medical vaporizer, portable medical vaporizer with a heat temperature modification, and preparation for nebulizer in a paste or powder. The delivery system may be a device and drug system capable of delivering a fixed-dose combination of drugs in a regimen.

In one embodiment, the invention provides a kit for treating or preventing a condition in a patient, the kit comprising: (a) a pharmaceutical composition in a therapeutically effective amount; and (b) at least one blister package, a lidded blister, a blister card or packet, a clamshell, an intravenous (IV) package, an IV packette, or an IV container a tray or a shrink wrap comprising the pharmaceutical composition and instructions for using the pharmaceutical composition.

In one embodiment, the invention provides a method of treating and/or preventing a COVID-19 viral condition in a patient comprising: selecting a patient in need of treating and/or preventing a viral condition; and administering to the patient at least one active agent selected from the group consisting of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection with COVID-19.

In one embodiment, the invention provides a method of treating and/or preventing a viral condition caused by COVID-19 in a patient comprising: selecting the patient in need of treating and/or preventing a viral condition; and administering at least one active agent selected from the group consisting of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, wherein the viral condition is to mitigate infections with COVID-19 by reducing their transmissibility and duration or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection.

In one embodiment, the invention provides a method of treating and/or preventing a viral condition of COVID-19 in a patient comprising: selecting a patient in need of treating and/or preventing a viral condition; and administering to the patient at least one active agent selected from the group consisting of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, wherein the viral condition is to prevent acute viral infection from becoming chronic active or latent infection.

In one embodiment, the present invention provides a pharmaceutical composition comprising: a therapeutically effective amount of one or more of dexamethasone, mifepristone, relacorilant, miricorilant, valsartan, rupintrivir, ritonavir, myricetin, rifampin, remdesivir, remdesivir ribose alcohol active metabolite GS-441524, hydroxychloroquine, pharmaceutically acceptable salts thereof, and combinations thereof, and at least one additional active anti-viral agent selected from the group consisting of molecules with potential to bind viral PS, annexin-5, anti-PS monoclonal or polyclonal antibodies, bavituximab, and viral glucocorticoid response elements (GREs), Mifepristone derivatives, cell entry inhibitors, un-coating inhibitors, reverse transcriptase inhibitors, integrase inhibitors, transcription inhibitors, anti-sense translation inhibitors, ribozyme translation inhibitors, prion processing and targeting inhibitors, protease inhibitors, assembly inhibitors, release phase inhibitors, immuno-system modulators, and vaccines. Suitable anti-viral agents include, but are not limited to Abacavir, Aciclovir, Acyclovir, Adefovir, Alferon LDO, Amantadine, Amdoxovir, Ampligen, Amprenavir, Aplaviroc, Apricitabine, Arbidol, Atazanavir, Ateviridine, Atripla, Balavir, Bevirimat, BILN 2061, Brecanavir, Brivudine, Calanolide A, Capravirine, Cidofovir, Combivir, Condylox, Cyanovirin-N, Darunavir, Delavirdine, Dexelvucitabine, Diarylpyrimidines, Didanosine, Docosanol, Dolutegravir, Ecoliever, Edoxudine, Efavirenz, Elvitegravir, Elvucitabine, Emivirine, Emtricitabine, Enfuvirtide, Entecavir, Epigallocatechin gallate, Etravirine, Famciclovir, Fialuridine, Fomivirsen, Fosamprenavir, Foscarnet, Fosfonet, Fusion inhibitor, Ganciclovir, Gardasil, Globoidnan A, GritTithsin, GS-9137, Ibacitabine, Ibalizumab, Immunovir, Idoxuridine, Imiquimod, Indinavir, Inosine, Interferon gamma, Interferon type III, Interferon type II, Interferon type I, Interferon, Integrase inhibitor, Kivexa/Epzicom, Lamivudine, Lodenosine, Lopinavir, Loviride, MK-0518, Maraviroc, Miltefosine, Moroxydine, Methisazone, Peginterferon alfa-2a, Penciclovir, Peramivir, Pleconaril, Podophyllotoxin, Portmanteauinhibitors, PRO 140, Protease inhibitor, Quinotaline, Racivir, Raltegravir, Reverse transcriptase inhibitor, Ribavirin, Rilpivirine, Rimantadine, Ritonavir, R-roscovitine, Pyramidine, Saquinavir, SCH 503034, Sofosbuvir, Stampidine, Stavudine, Synergistic enhancer, Taribavirin, Tea tree oil, Telaprevir, Telbivudine, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Vivecon, VX 950/Telaprevir, Zalcitabine, Zanamivir, Ziagen, and Zidovudine.

In one embodiment, the composition according to the present invention can be co-administered to an individual in need thereof in combination with one or more antiviral drugs. Suitable antiviral drugs include, but are not limited to, Abacavir, Aciclovir, Acyclovir, Adefovir, Alferon LDO, Amantadine, Amdoxovir, Ampligen, Amprenavir, Aplaviroc, Apricitabine, Arbidol, Atazanavir, Ateviridine, Atripla, Bevirimat, BILN 2061, Brecanavir, Brivudine, Calanolide A, Capravirine, Cidofovir, Combivir, Condylox, Cyanovirin-N, Darunavir, Delavirdine, Dexelvucitabine, Diarylpyrimidines, Didanosine, Docosanol, Edoxudine, Efavirenz, Elvitegravir, Elvucitabine, Emivirine, Emtricitabine, Enfuvirtide, Entecavir, Epigallocatechin gallate, Etravirine, Famciclovir, Fialuridine, Fomivirsen, Fosamprenavir, Foscamet, Fosfonet, Fusion inhibitor, Ganciclovir, Gardasil, Globoidnan A, Griffithsin, GS-9137, Ibacitabine, Ibalizumab, Immunovir, Idoxuridine, Imiquimod, Indinavir, Inosine, Interferongamma, Interferon type III, Interferon type II, Interferon type I, Interferon, Lamivudine, Lodenosine, Lopinavir, Loviride, MK-0518, Maraviroc, Miltefosine, Moroxydine, Nelfinavir, Nevirapine, Nexavir, Oragen, Oseltamivir, Penciclovir, Peramivir, Pleconaril, Podophyllotoxin, Portmanteau inhibitors, PRO 140, Quinotaline, Racivir, Raltegravir, Ribavirin, Rilpivirine, Rimantadine, Ritonavir, R-roscovitine, Saquinavir, SCH 503034, Stampidine, Stavudine, Taribavirin, Telbivudine, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Vivecon, VX 950/Telaprevir, Zalcitabine, Zanamivir, and Zidovudine (AZT).

In one embodiment, the present invention provides a pharmaceutical composition comprising: a therapeutically effective amount of one or more of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, and, to address potential co-morbid super-infections along with COVID-19, at least one antibacterial agent. Suitable antibacterial agents include, but are not limited to, Aztreonam, Chlorhexidine Gluconate, Imidurea, Lycetamine, Nibroxane, Pirazmonam Sodium, Propionic Acid, Pyrithione Sodium, Sanguinarium Chloride, Tigemonam Dicholine, Acedapsone, Acetosulfone Sodium, Alamecin, Alexidine, Amdinocillin, Amdinocillin Pivoxil, Amicycline, Amifloxacin, Amifloxacin Mesylate, Amikacin, Amikacin Sulfate, Aminosalicylic acid, Aminosalicylate sodium, Amoxicillin, Amphomycin, Ampicillin, Ampicillin Sodium, Apalcillin Sodium, Apramycin, Aspartocin, Astromicin Sulfate, Avilamycin, Avoparcin, Azithromycin, Azlocillin, Azlocillin Sodium, Bacampicillin Hydrochloride, Bacitracin, Bacitracin Methylene Disalicylate, Bacitracin Zinc, Bambermycins, Benzoylpas Calcium, Berythromycin, Betamicin Sulfate, Biapenem, Biniramycin, Biphenamine Hydrochloride, Bispyrithione Magsulfex, Butikacin, Butirosin Sulfate, Capreomycin Sulfate, Carbadox, Carbenicillin Disodium, Carbenicillin Indanyl Sodium, Carbenicillin Phenyl Sodium, Carbenicillin Potassium, Carumonam Sodium, Cefaclor, Cefadroxil, Cefamandole, Cefamandole Nafate, Cefamandole Sodium, Cefaparole, Cefatrizine, Cefazaflur Sodium, Cefazolin, Cefazolin Sodium, Cefbuperazone, Cefdinir, Cefepime, Cefepime Hydrochloride, Cefetecol, Cefixime, Cefinenoxime Hydrochloride, Cefinetazole, Cefinetazole Sodium, Cefonicid Monosodium, Cefonicid Sodium, Cefoperazone Sodium, Ceforanide, Cefotaxime Sodium, Cefotetan, Cefotetan Disodium, Cefotiam Hydrochloride, Cefoxitin, Cefoxitin Sodium, Cefpimizole, Cefpimizole Sodium, Cefpiramide, Cefpiramide Sodium, Cefpirome Sulfate, Cefpodoxime Proxetil, Cefprozil, Cefroxadine, Cefsulodin Sodium, Ceftazidime, Ceftibuten, Ceftizoxime Sodium, Ceftriaxone Sodium, Cefuroxime, Cefuroxime Axetil, Cefuroxime Pivoxetil, Cefuroxime Sodium, Cephacetrile Sodium, Cephalexin, Cephalexin Hydrochloride, Cephaloglycin, Cephaloridine, Cephalosporin, Cephalothin Sodium, Cephapirin Sodium, Cephradine, Cetocycline Hydrochloride, Cetophenicol, Chloramphenicol, Chloramphenicol Palmitate, Chloramphenicol Pantothenate Complex, Chloramphenicol Sodium Succinate, Chlorhexidine Phosphanilate, Chloroxylenol, Chlortetracycline Bisulfate, Chlortetracycline Hydrochloride, Cinoxacin, Ciprofloxacin, Ciprofloxacin Hydrochloride, Cirolemycin, Clarithromycin, Clinafloxacin Hydrochloride, Clindamycin, Clindamycin Hydrochloride, Clindamycin Palmitate Hydrochloride, Clindamycin Phosphate, Clofazimine, Cloxacillin Benzathine, Cloxacillin Sodium, Cloxyquin, Colistimethate Sodium, Colistin Sulfate, Coumermycin, Coumermycin Sodium, Cyclacillin, Cycloserine, Dalfopristin, Dapsone, Daptomycin, Demeclocycline, Demeclocycline Hydrochloride, Demecycline, Denofungin, Diaveridine, Dicloxacillin, Dicloxacillin Sodium, Dihydrostreptomycin Sulfate, Dipyrithione, Dirithromycin, Doxycycline, Doxycycline Calcium, Doxycycline Fosfatex, Doxycycline Hyclate, Droxacin Sodium, Enoxacin, Epicillin, Epitetracycline Hydrochloride, Erythromycin, Erythromycin Acistrate, Erythromycin Estolate, Erythromycin Ethylsuccinate, Erythromycin Gluceptate, Erythromycin Lactobionate, Erythromycin Propionate, Erythromycin Stearate, Ethambutol Hydrochloride, Ethionamide, Fleroxacin, Floxacillin, Fludalanine, Flumequine, Fosfomycin, Fosfomycin Tromethamine, Fumoxicillin, Furazolium Chloride, Furazolium Tartrate, Fusidate Sodium, Fusidic Acid, Gentamicin Sulfate, Gloximonam, Gramicidin, Haloprogin, Hetacillin, Hetacillin Potassium, Hexedine, Ibafloxacin, Imipenem, Isoconazole, Isepamicin, Isoniazid, Josamycin, Kanamycin Sulfate, Kitasamycin, Levofuraltadone, Levopropylcillin Potassium, Lexithromycin, Lincomycin, Lincomycin Hydrochloride, Lomefloxacin, Lomefloxacin Hydrochloride, Lomefloxacin Mesylate, Loracarbef, Mafenide, Meclocycline, Meclocycline Sulfosalicylate, Megalomicin Potassium Phosphate, Mequidox, Meropenem, Methacycline, Methacycline Hydrochloride, Methenamine, Methenamine Hippurate, Methenamine Mandelate, Methicillin Sodium, Methoprim, Metronidazole Hydrochloride, Metronidazole Phosphate, Mezlocillin, Mezlocillin Sodium, Minocycline, Minocycline Hydrochloride, Mirincamycinlydrochloride, Monensin, Monensin Sodium, Nafcillin Sodium, Nalidixate Sodium, Nalidixic Acid, Natamycin, Nebramycin, Neomycin Palmitate, Neomycin Sulfate, Neomycin Undecylenate, Netilmicin Sulfate, Neutramycin, Nifuradene, Nifuraldezone, Nifuratel, Nifuratrone, Nifurdazil, Nifurimide, Nifurpirinol, Nifurquinazol, Nifurthiazole, Nitrocycline, Nitrofurantoin, Nitromide, Norfloxacin, Novobiocin Sodium, Ofloxacin, Ormethoprim, Oxacillin Sodium, Oximonam, Oximonam Sodium, Oxolinic Acid, Oxytetracycline, Oxytetracycline Calcium, Oxytetracycline Hydrochloride, Paldimycin, Parachlorophenol, Paulomycin, Pefloxacin, Pefloxacin Mesylate, Penamecillin, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentizidone Sodium, Phenyl Aminosalicylate, Piperacillin Sodium, Pirbenicillin Sodium, Piridicillin Sodium, Pirlimycin Hydrochloride. Pivampicillin Hydrochloride, Pivampicillin Pamoate, Pivampicillin Probenate, Polymyxin B Sulfate, Porfiromycin, Propikacin, Pyrazinamide, Pyrithione Zinc, Quindecamine Acetate, Quinupristin, Racephenicol, Ramoplanin, Ranimycin, Relomycin, Repromicin, Rifabutin, Rifametane, Rifamexil, Rifamide, Rifampin, Rifapentine, Rifaximin, Rolitetracycline, Rolitetracycline Nitrate, Rosaramicin, Rosaramicin Butyrate, Rosaramicin Propionate, Rosaramicin Sodium Phosphate, Rosaramicin Stearate, Rosoxacil, Roxarsone, Roxithromycin, Sancycline, Sanfetrinem Sodium, Sarmoxicillin, Sarpicillin, Scopafungin, Sisomicin, Sisomicin Sulfate, Sparfloxacin, Spectinomycin Hydrochloride, Spiramycin, Stallimycin Hydrochloride, Steffimycin, Streptomycin Sulfate, Streptonicozid, Sulfabenz, Sulfabenzamide, Sulfacetamide, Sulfacetamide Sodium, Sulfacytine, Sulfadiazine, Sulfadiazine Sodium, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, Sulfasalazine, Sulfasomizole, Sulfathiazole, Sulfazamet, Sulfisoxazole, Sulfisoxazole Acetyl, Sulfisoxazole Diolamine, Sulfomyxin, Sulopenem, Sultamicillin, Suncillin Sodium, Talampicillin Hydrochloride, Teicoplanin, Temafiloxacin Hydrochloride, Temocillin, Tetracycline, Tetracycline Hydrochloride, Tetracycline Phosphate Complex, Tetroxoprim, Thiamphenicol, Thiphencillin Potassium, Ticarcillin Cresyl Sodium, Ticarcillin Disodium, Ticarcillin Monosodium, Ticlatone, Tiodonium Chloride, Tobramycin, Tobramycin Sulfate, Tosufloxacin, Trimethoprim, Trimethoprim Sulfate, Trisulfapyrimidines, Troleandomycin, Trospectomycin Sulfate, Tyrothricin, Vancomycin, Vancomycin Hydrochloride, Virginiamycin, Zorbamycin, Difloxacin Hydrochloride, Lauryl Isoquinolinium Bromide, Moxalactam Disodium, Ornidazole, Pentisomicin, and Sarafloxacin Hydrochloride.

In one embodiment, the composition according to the present invention can be co-administered to an individual in need thereof in combination with one or more antibiotics. Suitable antibiotics include, but are not limited to, Amikacin disulfate salt, Amikacin hydrate, Anisomycin from *Streptomyces griseolus*, Apramycin sulfate salt, Azithromycin, Blasticidine S hydrochloride, Brefeldin A, Brefeldin A from *Penicillium brefeldianum*, Butirosin sulfate salt, Butirosin A from *Bacillus vitellinus*, Chloramphenicol, Chloramphenicol base, Chloramphenicol succinate sodium salt, Chlortetracycline hydrochloride, Chlortetracycline hydrochloride from *Streptomyces aureofaciens*, Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus*, Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea*, Gentamicin sulfate salt, Gentamicin sulfate salt powder USP, Gentamicin-Glutamine solution liquid, Helvolic acid from *Cephalosporium caerulens*, Hygromycin B *Streptomyces hygroscopicus*, Hygromycin B *Streptomyces hygroscopicus* powder, Hygromycin B solution *Streptomyces hygroscopicus*, Josamycin, Josamycin solution, Kanamycin B sulfate salt, Kanamycin disulfate salt from *Streptomyces kanamyceticus*, Kanamycin monosulfate from *Streptomyces kanamyceticus*, Kanamycin monosulfate from *Streptomyces kanamyceticus* powder USP, Kanamycin solution from *Streptomyces kanamyceticus*, Kirromycin from *Streptomyces collinus*, Lincomycin hydrochloride, Lincomycin standard solution, Meclocycline sulfosalicylate salt, Mepartricin, Midecamycin from *Streptomyces mycarofaciens*, Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger*, Rapamycin from *Streptomyces hygroscopicus*, Ribostamycin sulfate salt, Rifampicin, Rifamycin SV sodium salt, Rosamicin *Micromonospora rosaria*, Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus*, Tobramycin. Tobramycin sulfate salt, Tunicamycin A1 homolog, Tunicamycin C2 homolog, Tunicamycin *Streptomyces* sp., Tylosin solution, Tylosin tartrate, Viomycin sulfate salt, Virginiamycin M1, (S)-(+)-Camptothecin, 10-Deacetylbaccatin III from *Taxus baccata*, 5-Azacytidine, 7-Aminoactinomycin D, 8-Quinolinol crystalline, 8-Quinolinol hemisulfate salt crystalline, 9-Dihydro-13-acety Ibaccatin III from *Taxus canadensis*, Aclarubicin, Aclarubicin hydrochloride, Actinomycin D from *Streptomyces* sp., Actinomycin I from *Streptomyces antibioticus*, Actinomycin V from *Streptomyces antibioticus*, Aphidicolin Nigrosporasphaerica, Batilomycin A1 from *Streptomyces griseus*, Bleomycin sulfate from *Streptomyces verticillus*, Capreomycin sulfate from *Streptomyces capreolus*, Chromomycin A3 *Streptomyces griseus*, Cinoxacin, Ciprofloxacin BioChemika, cis-Diammineplatinum (II) dichloride, Coumermycin A1, Cytochalasin B *Helminthosporium dematioideum*, Cytochalasin D *Zygosporium mansonii*, Dacarbazine Daunombicin hydrochloride, Daunorubicin hydrochloride USP, Distamycin A hydrochloride from *Streptomyces distallicus*, Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus*, Ganciclovir, Gliotoxin from *Gliocladium fimbriatum*, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptoniyces flocculus* Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt, *Bacillus licheniformis*, Carbenicillin disodium salt, Cefaclor, Cefamandole lithium salt, Cefamandole nafate, Cefamandole sodium salt, Cefazolin sodium salt, Cefinetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine. Cloxacillin sodium salt, Cloxacillin sodium salt monohydrate, D-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from *Staphylococcus staphylolyticus*, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycinmonosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi(calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus colistinus*, Colistin sulfate salt, Econazole nitrate salt, Hydrocortisone 21-acetate, Filipin complex *Streptomyces filipinensis*, Gliotoxin from *Gliocladium timbriatum*, Gramicidin A from *Bacillus brevis*, Gramicidin C from *Bacillus brevis*, Gramicidin from *Bacillus* aneurinolyticus (*Bacillus brevis*), lonomycin calcium salt *Streptomyces conglobatus*, Lasalocid A sodium salt, Lonomycin A sodium salt from *Streptomyces ribosidificus*, Monensin sodium salt, N-(6-Aminohexyl)-5-chloro-1-naphthalenesulfonamide hydrochloride, Narasin from *Streptomyces auriofaciens*, Nigericin sodium salt from *Streptomyces hygroscopicus*, Nisin from *Streptococcus lactis*, Nonactin from *Streptomyces* sp., Nystatin, Nystatin powder, Phenazine methosulfate, Pimaricin, Pimaricin from *Streptomyces chattanoogensis*, Polymyxin B solution. Polymyxin B sulfate salt DL-Penicillamine acetone adduct hydrochloride monohydrate, Polymyxin B sulfate salt powder ISP, Praziquantel, Salinomycin from *Streptomyces albus*, Salinomycin from *Streptomyces albus*, Surfactin from *Bacillus subtilis*, Valinomycin, (+)-Usnic acid from *Usnea dasypoga*, (±)-Miconazole nitrate salt, (S)-(+)-Camptothecin, 1-Deoxymannojirimycin hydrochloride, i-Deoxynojirimycin hydrochloride, 2-Heptyl-4-hydroxyquinoline N-oxide, Cordycepin, 1,10-Phenanthroline hydrochloride monohydrate puriss., 6-Diazo-5-oxo-L-norleucine, 8-Quinolinol crystalline, 8-Quinolinol hemisulfate salt, Antimycin A from *Streptomyces* sp., Antimycin A1, Antimycin A2, Antimycin A3, Antipain, Ascomycin, Azaserine, Bafilomycin A1 from *Streptomyces griseus*, Bafilomycin B1 from *Streptomyces* species, Cerulenin BioChemika, Chloroquine diphosphate salt, Cinoxacin, Ciprofloxacin, Mevastatin BioChemika, Concanamycin A, Concanamycin A *Streptomyces* sp., Concanamycin C from *Streptomyces* species, CoumermycinA1, Cyclosporin A from *Tolypocladium injlatum*, Cyclosporin A, Econazole nitrate salt, Enrofloxacin, Etoposide, Flumequine, Formycin A, Furazolidone, Fusaric acid from *Gibberella fujikuroi*, Geldanamycin from *Streptomyces hygroscopicus*, Gliotoxin from *Gliocladium fimbriatum*, Gramicidin A from *Bacillus brevis*, Gramicidin C from *Bacillus brevis*, Gramicidin from *Bacillus* aneurinolyticus (*Bacillus brevis*), Gramicidin from *Bacillus brevis*, Herbimycin A from *Streptomyces hygroscopicus*, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z *Streptomyces tendae*, N-Methyl-1-deoxynojirimycin, Nogalamycin from *Streptomyces nogalater*, Nonactin D80% from *Streptomyces tsusimaensis*, Nonactin from *Streptomyces* sp., Novobiocin sodium salt, Ofloxacin, Oleandomycin triacetate, Oligomycin *Streptomyces diastatochromogenes*, Oligomycin A, Oligomycin B, Oligomycin C, Oligomycin *Streptomyces diastatochromogenes*, Oxolinic acid, Piericidin A from *Streptomyces mobaraensis*, Pipemidic acid, Radicicol from *Diheterospora chlamydosporia* solid, Rapamycin from *Streptomyces hygroscopicus*, Rebeccamycin from *Saccharothrix aerocolonigenes*, Sinefungin, Staurosporine *Streptomyces* sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from *Streptomyces* sp., Trimethoprim, Trimethoprim lactate salt, Vineomycin A1 from *Streptomyces albogriseolus* subsp., *Tectorigenin*, and Paracelsin *Trichoderma reesei*.

In one embodiment, the present invention provides a pharmaceutical composition comprising a therapeutically effective amount of one or more of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, and, to address potential co-morbid super-infections along with COVID-19, at least one anti-fungal agent. Suitable anti-fungal agents include, but are not limited to, polyene antimycotics such as Natamycin, Rimocidin, Filipin, Nystatin, Amphotericin B, and Candicin, imidazole and triazole antifungal drugs such as Imidazoles like Miconazole (Miconazole nitrate), Ketoconazole, Clotrimazole (marketed as Lotrimin, Canesten in the UK), Econazole, Bifonazole, Butoconazole, Fenticonazole, Isoconazole, Oxiconazole, Sertaconazole (marketed as Ertaczo), Sulconazole, Tioconazole, Fluconazole, Itraconazole, Isavuconazole, Ravuconazole, Posaconazole, Voriconazole, and Terconazole. Allylamines such as Terbinafine (marketed as Lamisil), Amorolfine, Naftifine (marketed as Naftin), and Butenafine (marketed as Lotrimin Ultra), Echinocandins such as Anidulafungin, Caspofungin, and Micafungin, Benzoic acid in combination with a keratolytic agent (such as in Whitfield's Ointment), Ciclopirox olamine, Flucytosine, or 5-fluorocytosine, Griseofulvin, and Gentian Violet Haloprogin Tolnaftate (marketed as Tinactin, Desenex, Aftate).

In one embodiment, the present invention provides a pharmaceutical composition comprising a therapeutically effective amount of one or more of dexamethasone, mifepristone, relacorilant, miricorilant, valsartan, rupintrivir, ritonavir, myricetin, rifampin, remdesivir, remdesivir active metabolite GS-441524, hydroxychloroquine, pharmaceutically acceptable salts thereof, and combinations thereof, and, to address potential co-morbid super-infections along with COVID-19, at least one anti-parasitic agent. Suitable anti-parasitic agents include, but are not limited to, Antinematodes such as Mebendazole (for most nematode infections), Pyrantel pamoate (for most nematode infections), Thiabendazole (for roundworm infections), and Diethycarbazine (for treatment of Lymphatic filariasis), one or more antiparasitic drugs that comprises Anticestodes such as Niclosamide (for tapeworm infections), and Praziquantel (for tapeworm infections), Antitrematodes such as Praziquantel, Antiamoebics such as Rifampin, Amphotericin B, Clioquinol, Iodoquinol Metronidazole, Tinidazole, Ornidazole, Secnidazole Atovaquone, Emetine, Fumagillin, and Trimetrexate, Antiprotozoals such as Amphotericin, Antimony, Eflornithine, Furazolidone, Melarsoprol, Metronidazole, Miltefosine (Impavido), Omidazole, Paromomycin sulfate, Pentamidine, Pyrimethamine, and Tinidazole.

In one embodiment, the invention provides a pharmaceutical composition comprising: i) a first therapeutic agent comprising at least one antiviral agent or pharmaceutically acceptable salt thereof selected from an ARB such as Valsartan, a PI such as Rupintrivir or Ritonavir, an RdRpI such as Myricetin, Rifampin, Remdesivir or its ribose alcohol active metabolite GS-441524, an MRI such as Hydroxychloroquine, pharmaceutically acceptable salts thereof, and combinations thereof; ii) a second therapeutic agent comprising a PSI that is a GCR modulator/antagonist selected from the group consisting of Dexamethasone, Mifepristone, Relacorilant, Miricorilant, pharmaceutically acceptable salts thereof, and combinations thereof; and iii) at least one pharmaceutically acceptable carrier, wherein the pharmaceutical composition is formulated as a liquid, elixir, aerosol, gas, spray, powder, tablet, pill, capsule, gel, geltab, nano-suspension, nano-particle, extended release dosage form, or a topical formulation, and wherein the antiviral agents are each present in an amount which, in combination, is therapeutically effective for treating or preventing a viral infection in a patient. In certain embodiments, the one or more antiviral agents in this pharmaceutical composition are active against COVID-19.

In one embodiment, the invention provides a pharmaceutical composition comprising: i) a first therapeutic agent comprising at least one antiviral agent or pharmaceutically acceptable salt thereof selected from an ARB such as Valsartan, a PI such as Rupintrivir or Ritonavir, an RdRpI such as Myricetin, Rifampin, Remdesivir or its ribose alcohol active metabolite GS-441524, and combinations thereof; ii) a second therapeutic agent comprising an MRI such as Hydroxychloroquine or a pharmaceutically acceptable salt thereof; and iii) at least one pharmaceutically acceptable carrier, wherein the pharmaceutical composition is formulated or manufactured as a liquid, elixir, aerosol, spray, powder, tablet, pill, capsule, gel, geltab, nano-suspension, nano-particle, extended release dosage form, or a topical formulation, and wherein the antiviral agents are each present in an amount which, in combination, is therapeutically effective for treating or preventing a viral infection in a patient. In certain embodiments, the one or more antiviral agents in this pharmaceutical composition are active against COVID-19.

In one embodiment, the invention provides a pharmaceutical composition comprising: i) a first therapeutic agent comprising least one antiviral agent or pharmaceutically acceptable salt thereof selected from an ARB such as Valsartan, a PI such as Rupintrivir or Ritonavir, and combinations thereof; ii) a second therapeutic agent comprising an RdRpI such as Myricetin, Rifampin, Remdesivir or its ribose alcohol active metabolite GS-441524, pharmaceutically acceptable salts thereof, and combinations thereof; and iii) at least one pharmaceutically acceptable carrier, wherein the pharmaceutical composition is formulated as a liquid, elixir, aerosol, gas, spray, powder, tablet, pill, capsule, gel, geltab, nano-suspension, nano-particle, extended release dosage form, or a topical formulation, and wherein the antiviral agents are each present in an amount which, in combination, is therapeutically effective for treating or preventing a viral infection in a patient. In certain embodiments, the one or more antiviral agents in this pharmaceutical composition are active against COVID-19.

In one embodiment, the invention provides a pharmaceutical composition comprising: i) a first therapeutic agent comprising at least one antiviral agent or pharmaceutically acceptable salt thereof selected from an ARB such as Valsartan; ii) a second therapeutic agent comprising a P1 such as Rupintrivir or Ritonavir, pharmaceutically acceptable salts thereof, and combinations thereof; and iii) at least one pharmaceutically acceptable carrier, wherein the pharmaceutical composition is formulated as a liquid, elixir, aerosol, gas, spray, powder, tablet, pill, capsule, gel, geltab, nano-suspension, nano-particle, extended release dosage form, or a topical formulation, and wherein the antiviral agents are each present in an amount which, in combination, is therapeutically effective for treating or preventing a viral infection in a patient. In certain embodiments, the one or more antiviral agents in this pharmaceutical composition are active against COVID-19.

DETAILED DESCRIPTION OF THE INVENTION

As used herein, the term "effective amount" refers to an amount that is sufficient to result in the prevention of the development, recurrence, or onset of a disease or condition, such as neoplasia or infection, and one or more symptoms thereof, to enhance or improve the prophylactic effect(s) of another therapy, reduce the severity and/or duration of a disease or condition, such as viral infection, ameliorate one or more symptoms of a disease or condition such as infection, prevent the advancement of a disease or condition, such as infection, cause regression of a disease or condition, such as viral infection, and/or enhance or improve the therapeutic effect(s) of another therapy. An amount is "effective" as used herein, when the amount provides an effect in the subject.

As used herein, the phrase "pharmaceutically acceptable" means approved by a regulatory agency of a federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, such as neoplasia, viral infection, latent viral infections, or a symptom thereof in a subject resulting from the administration of a therapy (e.g, a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.), a primate, or a human. In some embodiments, the subject is a non-human animal such as a farm animal (e.g., a horse, pig, or cow) or a pet (e.g., a dog or cat).

As used herein, the terms "therapies" and "therapy" can refer to any method(s), composition(s), and/or agent(s) that can be used in the prevention, treatment and/or management of a disease or condition, such as neoplasia or viral infection, or one or more symptoms thereof. In certain embodiments, the terms "therapy" and "therapies" refer to chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a viral infection or one or more symptoms thereof.

As used herein, the terms "treat," "treatment," and "treating" in the context of the administration of a therapy to a subject refer to the reduction or inhibition of the progression and/or duration of a disease or condition, such as neoplasia or viral infection, the reduction or amelioration of the severity of a disease or condition, such as neoplasia or infection, and/or the amelioration of one or more symptoms thereof resulting from the administration of one or more therapies.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "agent" refers to any molecule, compound, methodology and/or substance for use in the prevention, treatment, management and/or diagnosis of viral disease.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, chemotherapy, and small molecule drugs.

As used herein, the terms "electronic cigarette," "e-cigarette," and "vape pen," in the context of the administration of a drug to a subject, refer to a battery-operated drug delivery device used to administer one or more doses of a pharmaceutical composition in the form of a vapor for the subject to inhale.

As used herein, the term "nebulizer," refers to a drug delivery device used to administer one or more doses of a pharmaceutical composition in the form of a mist for the subject to inhale. Nebulizers may use oxygen, compressed air, or ultrasonic power to break up solutions and suspensions into small aerosol droplets that can be directly inhaled from the mouthpiece of the device. An aerosol is suspension of solid or liquid particles in a gas. A nebulizer can be open to the air or a component of a closed system incorporated into a patient ventilator.

As used herein, the term "ARB," or "Angiotensin Receptor Blocker," refers to a class of drugs including azilsartan (Edarbi); candesartan (Atacand); eprosartan (Teveten); irbesartan (Avapro); telmisartan (Micardis), valsartan (Diovan); losartan (Cozaar), and, olmesartan (Benicar).

As used herein, the terms "glucocorticoid" and "glucocorticoid receptor modulator," refer to a group of drugs including, but not limited tobeclomethasone, betamethasone, budesonide, cortisone, dexamethasone, hydrocortisone, methylprednisolone, prednisolone, prednisone, and triamcinolone.

Phosphatidylserine (PS) binding represents an important inner membrane lipid in all human cells. PS represents a phospholipid, together with phosphatidylcholine (lecithin) and phosphatidylethanolamine (colamine-cephalin). PS is constructed of 1,2-diacylglycerol-3-phospho-L-serine. The 1,2-diacylglycerol-3-phosphate is also called phosphatidic acid, therefore the term "phosphatidyl". PS is normally exposed on human cells only in the case of apoptosis (programmed cell death, "voluntary cell suicide"). Enveloped viruses expose PS on their host-captured lipid bilayer membranes constantly. Enveloped viruses utilize this PS-exposure to evade attacks by the human immune system and to enter phagocytic cells like monocytes/macrophages.

3-O-sn-phosphatidyl-L-serine (PS):

The structure of a typical PS, as shown with stearic acid at position 1-O, and docosa-4,7,10,13,16,19-hexaenoic acid at position 2-O. This represents a major serine-cephalin from bovine brain. Fatty acid composition at position 1-O and 2-O is subject of variation, depending e.g. on cell type. The polar head group (phosphoserine) is negatively charged. The phosphate anion charge and the cation charge of the ammonium group neutralize each other. Therefore, PS is net-negatively charged at physiological pH 7.4.

Sn-Phosphatidylcholine (PC):

The structure of a typical PC, as shown with stearic acid at position 1-O, and linoleic acid at position 2-O. This represents a major lecithin from egg yolk and human cell membranes. Fatty acid composition at position 1-O and 2-O is subject of variation, depending, for example, on cell type. The polar head group (phosphocholine) is zwitterionic. The phosphate anion charge and the cation charge of the ammonium group neutralize each other. Therefore, PC is net-neutral at physiological pH 7.4. Most confirmed PS-Interception-Susceptible enveloped viruses are RNA viruses like COVID-19.

Formulations and Administration

The compounds and compositions of the present invention may be administered at therapeutically effective doses. In some embodiments, the compounds and compositions of the invention are administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In certain embodiments, the compounds of the invention are administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 190 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 425 mg/day, less than 450 mg/day, less than 475 mg/day, or less than 500 mg/day. In some embodiments, the compounds of the invention are administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 190 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 425 mg/day, more than 450 mg/day, more than 475 mg/day, or more than 500 mg/day.

The compounds and compositions of the present invention may be given once or more daily, or alternatively may be given with intervals of 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, or 12 weeks.

The compounds and compositions of the present invention may be given in an effective amount to an individual in need thereof. The amount of composition according to the present invention in one preferred embodiment is in the range of from about 0.01 milligram per kg body weight per dose to about 1000 milligram per kg body weight per dose, such as from about 0.01 milligram per kg body weight per dose to about 0.025 milligram per kg body weight per dose, for example from about 0.025 milligram per kg body weight per dose to about 0.05 milligram per kg body weight per dose, such as from about 0.05 milligram per kg body weight per dose to about 0.075 milligram per kg body weight per dose, for example from about 0.075 milligram per kg body weight per dose to about 0.1 milligram per kg body weight per dose, such as from about 0.1 milligram per kg body weight per dose to about 0.25 milligram per kg body weight per dose, such as from about 0.25 milligram per kg body weight per dose to about 0.5 milligram per kg body weight per dose, for example from about 0.5 milligram per kg body weight per dose to about 0.75 milligram per kg body weight per dose, such as from about 0.75 milligram per kg body weight per dose to about 1.0 milligram per kg body weight per dose, for example from about 1.0 milligram per kg body weight per dose to about 2.5 milligram per kg body weight per dose, such as from about 2.5 milligram per kg body weight per dose to about 5 milligram per kg body weight per dose, for example from about 5 milligram per kg body weight per dose to about 7.5 milligram per kg body weight per dose, such as from about 7.5 milligram per kg body weight per dose to about 10 milligram per kg body weight per dose, for example from about 10 milligram per kg body weight per dose to about 25 milligram per kg body weight per dose, such as from about 25 milligram per kg body weight per dose to about 50 milligram per kg body weight per dose, such as from about 50 milligram per kg body weight per dose to about 75 milligram per kg body weight per dose, for example from about 75 milligram per kg body weight per dose to about 100 milligram per kg body weight per dose, such as from about 100 milligram per kg body weight per dose to about 250 milligram per kg body weight per dose, for example from about 250 milligram per kg body weight per dose to about 500 milligram per kg body weight per dose, such as from about 500 milligram per kg body weight per dose to about 750 milligram per kg body weight per dose, for example from about 750 milligram per kg body weight per dose to about 1000 milligram per kg body weight per dose.

The compounds and compositions of the present invention may be given in the range of from about 0.01 milligram per kg body weight per dose to about 20 milligram per kg body weight per dose, such as from about 0.02 milligram per kg body weight per dose to about 18 milligram per kg body weight per dose, for example from about 0.04 milligram per kg body weight per dose to about 16 milligram per kg body weight per dose, such as from about 0.06 milligram per kg body weight per dose to about 14 milligram per kg body weight per dose, for example from about 0.08 milligram per kg body weight per dose to about 12 milligram per kg body weight per dose, such as from about 0.1 milligram per kg body weight per dose to about 10 milligram per kg body weight per dose, such as from about 0.2 milligram per kg body weight per dose to about 10 milligram per kg body weight per dose, for example from about 0.3 milligram per kg body weight per dose to about 10 milligram per kg body weight per dose, such as from about 0.4 milligram per kg body weight per dose to about 10 milligram per kg body weight per dose, for example from about 0.5 milligram per kg body weight per dose to about 10 milligram per kg body weight per dose, such as from about 0.6 milligram per kg body weight per dose to about 10 milligram per kg body weight per dose, for example from about 0.7 milligram per kg body weight per dose to about 10 milligram per kg body weight per dose, such as from about 0.8 milligram per kg body weight per dose to about 10 milligram per kg body weight per dose, for example from about 0.9 milligram per kg body weight per dose to about 10 milligram per kg body weight per dose, such as from about 1.0 milligram per kg body weight per dose to about 10 milligram per kg body weight per dose, for example from about 1.2 milligram per kg body weight per dose to about 10 milligram per kg body weight per dose, such as from about 1.4 milligram per kg body weight per dose to about 10 milligram per kg body weight per dose, for example from about 1.6 milligram per kg body weight per dose to about 10 milligram per kg body weight per dose, such as from about 1.8 milligram per kg body weight per dose to about 10 milligram per kg body weight per dose, for example from about 2.0 milligram per kg body weight per dose to about 10 milligram per kg body weight per dose, such as from about 2.2 milligram per kg body weight per dose to about 10 milligram per kg body weight per dose, for example from about 2.4 milligram per kg body weight per dose to about 10 milligram per kg body weight per dose, such as from about 2.6 milligram per kg body weight per dose to about 10 milligram per kg body weight per dose, for example from about 2.8 milligram per kg body weight per dose to about 10 milligram per kg body weight per dose, such as from about 3.0 milligram per kg body weight per dose to about 10 milligram per kg body weight per dose, for example from about 3.2 milligram per kg body weight per dose to about 10 milligram per kg body weight per dose, such as from about 3.4 milligram per kg body weight per dose to about 10 milligram per kg body weight per dose, for example from about 3.6 milligram per kg body weight per dose to about 10 milligram per kg body weight per dose, such as from about 3.8 milligram per kg body weight per dose to about 10 milligram per kg body weight per dose, for example from about 4.0 milligram per kg body weight per dose to about 10 milligram per kg body weight per dose, such as from about 4.2 milligram per kg body weight per dose to about 10 milligram per kg body weight per dose, for example from about 4.4 milligram per kg body weight per dose to about 10 milligram per kg body weight per dose, such as from about 4.6 milligram per kg body weight per dose to about 10 milligram per kg body weight per dose, for example from about 4.8 milligram per kg body weight per dose to about 10 milligram per kg body weight per dose, such as from about 5.0 milligram per kg body weight per dose to about 10 milligram per kg body weight per dose, for example from about 5.2 milligram per kg body weight per dose to about 10 milligram per kg body weight per dose, such as from about 5.4 milligram per kg body weight per dose to about 10 milligram per kg body weight per dose, for example from about 5.6 milligram per kg body weight per dose to about 10 milligram per kg body weight per dose, such as from about 5.8 milligram per kg body weight per dose to about 10 milligram per kg body weight per dose, for example from about 6.0 milligram per kg body weight per dose to about 10 milligram per kg body weight per dose, such as from about 6.2 milligram per kg body weight per dose to about 10 milligram per kg body weight per dose, for example from about 6.4 milligram per kg body weight per dose to about 10 milligram per kg body weight per dose, such as from about 6.6 milligram per kg body weight per dose to about 10 milligram per kg body weight per dose, for example from about 6.8 milligram per kg body weight per dose to about 10 milligram per kg body weight per dose, such as from about 7.0 milligram per kg body weight per dose to about 10 milligram per kg body weight per dose, for example from about 7.2 milligram per kg body weight per dose to about 10 milligram per kg body weight per dose, such as from about 7.4 milligram per kg body weight per dose to about 10 milligram per kg body weight per dose, for example from about 7.6 milligram per kg body weight per dose to about 10 milligram per kg body weight per dose, such as from about 7.8 milligram per kg body weight per dose to about 10 milligram per kg body weight per dose, for example from about 8.0 milligram per kg body weight per dose to about 10 milligram per kg body weight per dose, such as from about 0.2 milligram per kg body weight per dose to about 8 milligram per kg body weight per dose, for example from about 0.3 milligram per kg body weight per dose to about 8 milligram per kg body weight per dose, such as from about 0.4 milligram per kg body weight per dose to about 8 milligram per kg body weight per dose, for example from about 0.5 milligram per kg body weight per dose to about 8 milligram per kg body weight per dose, such as from about 0.6 milligram per kg body weight per dose to about 8 milligram per kg body weight per dose, for example from about 0.7 milligram per kg body weight per dose to about 8 milligram per kg body weight per dose, such as from about 0.8 milligram per kg body weight per dose to about 8 milligram per kg body weight per dose, for example from about 0.9 milligram per kg body weight per dose to about 8 milligram per kg body weight per dose, such as from about 1.0 milligram per kg body weight per dose to about 8 milligram per kg body weight per dose, for example from about 1.2 milligram per kg body weight per dose to about 8 milligram per kg body weight per dose, such as from about 1.4 milligram per kg body weight per dose to about 8 milligram per kg body weight per dose, for example from about 1.6 milligram per kg body weight per dose to about 8 milligram per kg body weight per dose, such as from about 1.8 milligram per kg body weight per dose to about 8 milligram per kg body weight per dose, for example from about 2.0 milligram per kg body weight per dose to about 8 milligram per kg body weight per dose, such as from about 2.2 milligram per kg body weight per dose to about 8 milligram per kg body weight per dose, for example from about 2.4 milligram per kg body weight per dose to about 8 milligram per kg body weight per dose, such as from about 2.6 milligram per kg body weight per dose to about 8 milligram per kg body weight per dose, for example from about 2.8 milligram per kg body weight per dose to about 8 milligram per kg body weight per dose, such as from about 3.0 milligram per kg body weight per dose to about 8 milligram per kg body weight per dose, for example from about 3.2 milligram per kg body weight per dose to about 8 milligram per kg body weight per dose, such as from about 3.4 milligram per kg body weight per dose to about 8 milligram per kg body weight per dose, for example from about 3.6 milligram per kg body weight per dose to about 8 milligram per kg body weight per dose, such as from about 3.8 milligram per kg body weight per dose to about 8 milligram per kg body weight per dose, for example from about 4.0 milligram per kg body weight per dose to about 8 milligram per kg body weight per dose, such as from about 4.2 milligram per kg body weight per dose to about 8 milligram per kg body weight per dose, for example from about 4.4 milligram per kg body weight per dose to about 8 milligram per kg body weight per dose, such as from about 4.6 milligram per kg body weight per dose to about 8 milligram per kg body weight per dose, for example from about 4.8 milligram per kg body weight per dose to about 8 milligram per kg body weight per dose, such as from about 5.0 milligram per kg body weight per dose to about 8 milligram per kg body weight per dose, for example from about 5.2 milligram per kg body weight per dose to about 8 milligram per kg body weight per dose, such as from about 5.4 milligram per kg body weight per dose to about 8 milligram per kg body weight per dose, for example from about 5.6 milligram per kg body weight per dose to about 8 milligram per kg body weight per dose, such as from about 5.8 milligram per kg body weight per dose to about 8 milligram per kg body weight per dose, for example from about 6.0 milligram per kg body weight per dose to about 8 milligram per kg body weight per dose, such as from about 0.2 milligram per kg body weight per dose to about 6 milligram per kg body weight per dose, for example from about 0.3 milligram per kg body weight per dose to about 6 milligram per kg body weight per dose, such as from about 0.4 milligram per kg body weight per dose to about 6 milligram per kg body weight per dose, for example from about 0.5 milligram per kg body weight per dose to about 6 milligram per kg body weight per dose, such as from about 0.6 milligram per kg body weight per dose to about 6 milligram per kg body weight per dose, for example from about 0.7 milligram per kg body weight per dose to about 6 milligram per kg body weight per dose, such as from about 0.8 milligram per kg body weight per dose to about 6 milligram per kg body weight per dose, for example from about 0.9 milligram per kg body weight per dose to about 6 milligram per kg body weight per dose, such as from about 1.0 milligram per kg body weight per dose to about 6 milligram per kg body weight per dose, for example from about 1.2 milligram per kg body weight per dose to about 6 milligram per kg body weight per dose, such as from about 1.4 milligram per kg body weight per dose to about 6 milligram per kg body weight per dose, for example from about 1.6 milligram per kg body weight per dose to about 6 milligram per kg body weight per dose, such as from about 1.8 milligram per kg body weight per dose to about 6 milligram per kg body weight per dose, for example from about 2.0 milligram per kg body weight per dose to about 6 milligram per kg body weight per dose, such as from about 2.2 milligram per kg body weight per dose to about 6 milligram per kg body weight per dose, for example from about 2.4 milligram per kg body weight per dose to about 6 milligram per kg body weight per dose, such as from about 2.6 milligram per kg body weight per dose to about 6 milligram per kg body weight per dose, for example from about 2.8 milligram per kg body weight per dose to about 6 milligram per kg body weight per dose, such as from about 3.0 milligram per kg body weight per dose to about 6 milligram per kg body weight per dose, for example from about 3.2 milligram per kg body weight per dose to about 6 milligram per kg body weight per dose, such as from about 3.4 milligram per kg body weight per dose to about 6 milligram per kg body weight per dose, for example from about 3.6 milligram per kg body weight per dose to about 6 milligram per kg body weight per dose, such as from about 3.8 milligram per kg body weight per dose to about 6 milligram per kg body weight per dose, for example from about 4.0 milligram per kg body weight per dose to about 6 milligram per kg body weight per dose, such as from about 4.2 milligram per kg body weight per dose to about 6 milligram per kg body weight per dose, for example from about 4.4 milligram per kg body weight per dose to about 6 milligram per kg body weight per dose, such as from about 4.6 milligram per kg body weight per dose to about 6 milligram per kg body weight per dose, for example from about 4.8 milligram per kg body weight per dose to about 6 milligram per kg body weight per dose, such as from about 5.0 milligram per kg body weight per dose to about 6 milligram per kg body weight per dose.

The compounds and compositions of the present invention may be administered enterally or through inhalation using devices including electronic cigarettes that may be single use or are provided with cartridges loaded with drug product (active pharmaceutical ingredients plus excipients) The compounds may be compressed into solid dosage units, such as pills or tablets, or be processed into capsules or suppositories. With the use of pharmaceutically suitable liquids the compounds can also be provided in the form of a solution, suspension, emulsion, e.g. for use as an injection preparation or eye drops, or as a spray, e.g. for use as a nasal spray. The compounds can also be prepared for use in open and closed system nebulizers and for delivery in cartridges placed into electronic cigarettes.

In one embodiment, the composition according to the present invention is administered to an individual in need thereof by way of a portable medical vaporizer including an electronic cigarette whereby the patient would receive a total daily dosage of BB-708, Plaquemdesivir, in a single use electronic cigarette or a drug product cartridge of a multi-use electronic cigarette, from about 60 milligrams to about 120 milligrams per day from 3 days to 14 days. Each electronic cigarette cartridge or single use electronic cigarette may contain 0.75 milliliters (mL) to 2.0 (mL) with a minimum weight per volume of BB-708 of 3 percent to 5 percent such that an average patient would consume all of the drug product in approximately 100 inhalations per (1 mL) cartridge pod or single use electronic cigarette or approximately 200 hundred inhalations for a 2 (mL) cartridge pod or higher capacity singe use electronic cigarette. The concentration of BB-708 can be adjusted upward to reduce the number of required inhalations to consume the prescribed dosage, for example, with the potential of 10 or fewer inhalations required with a higher concentration of BB-708 in the drug product. The dosage regimen may be adjusted within or outside of this range to provide the optimal therapeutic response and may be adjusted downward for pediatric usage and potentially upwards or downward depending on the body weight of the patient.

In one embodiment, the composition according to the present invention is administered to an individual in need thereof by way of a portable medical vaporizer including an electronic cigarette whereby the patient would receive a total daily dosage of BB-708B, Riboplaquemdesivir, in a single use electronic cigarette or a drug product cartridge of a multi-use electronic cigarette, from about 60 milligrams to about 120 milligrams per day from 3 days to 14 days. Each electronic cigarette cartridge or single use electronic cigarette may contain 0.75 milliliters (mL) to 2.0 (mL) with a minimum weight per volume of BB-708B of 3 percent to 5 percent such that an average patient would consume all of the drug product approximately 100 inhalations per (1 mL) cartridge pod or single use electronic cigarette or approximately 200 hundred inhalations for a 2 (mL) cartridge pod or higher capacity singe use electronic cigarette. The concentration of BB-708B can be adjusted upward to reduce the number of required inhalations to consume the prescribed dosage, for example, with potential of 10 or fewer inhalations required with a higher concentration of BB-708B in the drug product. The dosage regimen may be adjusted within or outside of this range to provide the optimal therapeutic response and may be adjusted downward for pediatric usage and potentially upwards or downward depending on the body weight of the patient.

In one embodiment, the composition according to the present invention is administered to an individual in need thereof by way of a portable medical vaporizer including an electronic cigarette whereby the patient would receive a total daily dosage of BB-710B. Ribodexadesivir, in a single use electronic cigarette or a drug product cartridge of a multi-use electronic cigarette, from about 60 milligrams to about 120 milligrams per day from 3 days to 14 days Each electronic cigarette cartridge or single use electronic cigarette may contain 0.75 milliliters (mL) to 2.0 (mL) with a minimum weight per volume of BB-710B of 3 percent to 5 percent such that an average patient would consume all of the drug product approximately 100 inhalations per (1 mL) cartridge pod or single use electronic cigarette or approximately 200 hundred inhalations for a 2 (mL) cartridge pod or higher capacity singe use electronic cigarette. The concentration of BB-710B can be adjusted upward to reduce the number of required inhalations to consume the prescribed dosage, for example, with potential of 10 or fewer inhalations required with a higher concentration of BB-710B in the drug product. The dosage regimen may be adjusted within or outside of this range to provide the optimal therapeutic response and may be adjusted downward for pediatric usage and potentially upwards or downward depending on the body weight of the patient.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers include lactose, starch, cellulose derivatives and the like, or mixtures thereof, used in suitable amounts.

Special Formulations for Alternate Specific Routes of Administration

The pharmaceutical compositions of the present invention may be optimized for particular types of delivery. For example, pharmaceutical compositions for oral delivery may be formulated using pharmaceutically acceptable carriers that are well known in the art. The carriers enable the agents in the composition to be formulated, for example, as a tablet, pill, capsule, solution, suspension, sustained release formulation, powder, liquid, or gel for oral ingestion by the subject, as well as a liquid containing vegetable glycerin or propylene glycol as vape carriers of actives.

The compounds of the present invention may also be delivered in an aerosol spray preparation from a pressurized pack, a nebulizer, a dry powder inhaler, or an electronic cigarette. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as described above. The compositions may be administered by the oral, intranasal, or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent, or positive pressure breathing machine Solution, suspension, or powder compositions may be administered orally or nasally from devices that deliver the formulation in an appropriate manner. Compositions for use in electronic cigarettes can be preloaded into cartridges for insertion into the vape pen body or in a single use unit.

The compounds of the present invention may be administered enterally, parenterally, or in a respiratory format, optionally mixed with pharmaceutically suitable auxiliaries, e.g., as described in the standard reference, Gennaro et al., Remington's Pharmaceutical Sciences. The compounds may be compressed into solid dosage units, such as pills or tablets, or be processed into capsules or suppositories. By means of pharmaceutically suitable liquids, the compounds can also be applied in the form of a solution, suspension, emulsion, e.g. for use as an injection preparation or eye drops, or as a spray, e.g. for use as a nasal spray.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, capsule, smart capsule, tablet, implant, troche, sachet, lozenge (minitablet), temporary or permanent suspension, ovule, suppository, wafer, chewable tablet, quick or fast dissolving tablet, effervescent tablet, buccal or sublingual solid, granule, film, sprinkle, pellet, bead, pill, powder, triturate, platelet, or strip. Compositions can also be administered as a "dry syrup" where the finished dosage form is placed directly on the tongue and swallowed or followed with a drink or beverage.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such solid carriers can be blended in a dosage form to achieve a desired performance. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended-release coating, or a targeted delayed release coating. These various coatings are known in the art, but for clarity, the following brief descriptions are provided seal coating, or coating with isolation layers. Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended-release coatings are designed to effect delivery over an extended period of time. The extended-release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended-release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, is a refined product obtained from the resinous secretion of an insect. This coating dissolves in media of pH>7.

Colorants, detackifiers, surfactants, antifoaming agents, lubricants, stabilizers such as hydroxypropylcellulose, acid/base may be added to the coatings besides plasticizers to solubilize or disperse the coating material, and to improve coating performance and the coated product.

In carrying out the methods of the present invention, the combination of the invention may be administered to mammalian species, such as dogs, cats, humans, etc. and as such may be incorporated in a conventional systemic dosage form, such as a tablet, capsule, elixir or injectable. The above dosage forms may also include at least one carrier material, excipient, lubricant, buffer, antibacterial, bulking agent (such as mannitol), antioxidants (ascorbic acid of sodium bisulfite) or the like.

Tablets of various sizes containing the active pharmaceutical ingredients can be prepared, e.g., of about 1 to 2000 mg in total weight, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending the compounds of the invention in a conventional liquid vehicle acceptable for pharmaceutical administration so as to provide the desired dosage.

In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin: an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

In one embodiment, there is provided a method of treating, preventing, or diagnosing a particular COVID-19 disease or condition by administering the disclosed compositions to a subject. In certain embodiments, the disclosed compositions are administered alone or can be included within a pharmaceutical composition.

Compositions of the present invention can include nanoparticles, composite nanoparticles, nanosuspension, or nano-capsules. In certain embodiments, pharmaceutical compositions may comprise, for example, at least about 0.1% of an active ingredient or nanoparticles, composite nanoparticles, or nano-capsules. In other embodiments, the active ingredient or nanoparticles, composite nanoparticles, or nano-capsules may comprise between about 2% to about 75% of the weight of the unit, or between about 25% to about 60%, and any range derivable therein.

The compositions of the present invention may also include various antioxidants to retard oxidation of one or more active ingredient or nanoparticles, composite nanoparticles, nanosuspension, or nano-capsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Packaging/Treatment Kits

The present invention relates to a kit for conveniently and effectively carrying out the methods in accordance with the present invention. Such kits may be suited for the delivery of solid oral forms such as tablets or capsules as well as inhaled dosage forms like electronic cigarettes that may require cartridges for drug product that can be used in appropriate devices. Such a kit may include one or more dosage units. Such kits can include a means for containing the dosages oriented in the order of their intended use. An example of a means for containing the dosages in the order of their intended uses is a card. Another example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid-day" and a PM dose; or an AM dose is packaged with a PM dose. The cards with blister may contain cartridges for electronic cigarettes.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat-sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising the compositions of the invention. Blister packs, clamshells or trays can be designed to be non-re-closable, so consumers can tell if a package has already opened. In one embodiment, a blister pack of the invention comprises a molded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one embodiment, a specialized form of a blister pack is a strip pack.

In one embodiment, a blister pack may also comprise a method of packaging where the compositions comprising combinations of ingredients of the invention are contained in between a card and a clear PVC layer. The PVC can be transparent so the item (pill, tablet, geltab, etc.) can be seen and examined easily. In one embodiment, the blister pack may be vacuum-formed around a mold so it can contain the compositions comprising combinations of ingredients of the invention snugly and have room to be opened upon purchase. In one embodiment, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. In embodiments with large items or multiple enclosed pills, tablets, geltabs, etc., the card may have a perforated window for access. In one embodiment, more secure blister packs, e.g., for items such as pills, tablets, geltabs, etc. of the invention may be used, and can comprise of two vacuum-formed PVC sheets meshed together at the edges, with the informative card inside.

In one embodiment, blister packaging may comprise at least two components (e.g., is a multi-ingredient combination of drugs of the invention) a thermoformed "blister" which houses the product (e.g., a pharmaceutical combination of the invention), and then a "blister card" that is a printed card with an adhesive coating on the front surface. During the assembly process, the blister component, which is most commonly made out of PVC, may be attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, 111.) using regular heat seal tooling.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one embodiment, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a childproof peel open security laminate. In one embodiment, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one embodiment, hermetically-sealed high barrier aluminum (e.g., alufoil) laminates are used. In one embodiment, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or day-minder to further help the patient to remember when to take a dosage or when a dosage has been taken.

Administration

The pharmaceutical compositions of the present invention may be optimized for particular types of delivery. For example, pharmaceutical compositions for oral delivery are formulated using pharmaceutically acceptable carriers that are well known in the art. The carriers enable the agents in the composition to be formulated, for example in respiratory and oral formats, as a vaping liquid, a tablet, pill, capsule, solution, suspension, sustained release formulation; powder, liquid or gel for oral ingestion by the subject.

The pharmaceutical compositions may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner. Electronic vaporizers like e-cigarettes may be single use containing drug product or multiple use taking prefilled cartridges of drug product containing active pharmaceutical ingredients and excipients including carriers.

In one embodiment, the compositions of the present invention may be administered repeatedly for a sustained period of time. In such embodiment, the dosage regimen will generally involve regular, such as daily, administration for a period of treatment of at least one month, or at least three months, or at least six months.

Alternatively, the compositions of the present invention may be applied intermittently, or in a pulsed manner. For example, the composition of the invention may be used for two or more days, stopped, then restarted again at a time from between 2 weeks to 3 months later, and at even more long-spaced intervals.

The routes of administration of a compound of the present invention will vary with the location and nature of the condition to be treated, and include, e.g., inhalation, intradermal, transdermal, parenteral, intravenous, intramuscular, intranasal, subcutaneous, percutaneous, intratracheal, intraperitoneal, perfusion, lavage, direct injection, and oral administration and formulation. As detailed below, the compounds in the present invention may be administered as medical gases by inhalation or intubation, as injectable liquids by intravascular, intravenous, intra-arterial, intracerobroventicular, intraperitoneal, subcutaneous administration, as topical liquids or gels, or in solid oral dosage forms.

The length of time of administration may vary depending on the type of biological matter (cell type, tissue type, organism genus and species, etc.) and/or its size (weight, surface area, etc.) and will depend in part upon dosage form and route of administration. In particular embodiments, a compound of the present invention may be provided for about or at least 30 seconds, 1 minute, 2 minutes, 3 minutes, 5 minutes, 10 minutes, 15 minutes, 30 minutes, 1 hour, 2 hours, 3 hours, four hours five hours, six hours, eight hours, twelve hours, twenty-four hours, or greater than twenty-four hours. The compounds of the present invention may be administered in a single dose or multiple doses, with varying amounts of time between administered doses.

The treatments may include various "unit doses." Unit dose is defined as containing a predetermined quantity of the therapeutic composition. The quantity to be administered, and the particular route and formulation, are within the skill of those in the clinical arts. A unit dose need not be administered as a single injection but may comprise continuous infusion over a set period of time. Alternatively, the amount specified may be the amount administered as the average daily, average weekly, or average monthly dose.

In one embodiment, the invention provides a topical pharmaceutical formulation for use in treatment of a subject comprising a composition of the invention and at least one pharmaceutically acceptable excipient. In such embodiment, the invention may provide a topical formulation wherein said formulation is in a form selected from the group consisting of: cream, lotion, gel, oil, ointment, suppository, spray, foam, liniment, aerosol, buccal and sublingual tablet or a transdermal device or patch for absorption through the skin or mucous membranes.

All references cited herein are incorporated herein by reference in their entireties.

While the present invention has been shown and described in connection with certain exemplary embodiments, it should be understood that these are exemplary of the invention and are not to be considered as limiting, and that it will be apparent to those skilled in the art that modifications and variations can be made without departing from the spirit and scope of the invention. Accordingly, it is not intended that the present invention be limited to the illustrated embodiments, but only by the appended claims.

What is claimed is:

1. A pharmaceutical composition for the treatment of COVID-19, comprising:
   a therapeutically effective amount of a first anti-viral agent consisting of a picornavirus 3C protease inhibitor or a pharmaceutically acceptable salt thereof,
   a therapeutically effective amount of a second anti-viral agent having a different mechanism of action consisting of ritonavir or a pharmaceutically acceptable salt thereof, and
   a third anti-viral agent selected from the group consisting of dexamethasone and remdesivir.

2. The pharmaceutical composition of claim 1, wherein the picornavirus 3C protease inhibitor is rupintrivir or a pharmaceutically acceptable salt thereof.

3. The pharmaceutical composition of claim 1, wherein the first anti-viral agent and the second anti-viral agent are provided as separate fixed solid oral dosage forms.

4. The pharmaceutical composition of claim 3, wherein the solid oral dosage forms are tablets.

5. The pharmaceutical composition of claim 3, wherein the first anti-viral agent is present in a first solid oral dosage form in an amount of about 100 mg to about 1500 mg, and the second anti-viral agent is present in a second solid oral dosage form in an amount of about 100 mg to about 1000 mg.

6. The pharmaceutical composition of claim 3, wherein the first anti-viral agent is present in a first solid oral dosage form in an amount of about 150 mg to about 300 mg, and the second anti-viral agent is present in a second solid oral dosage form in an amount of about 100 mg.

7. A kit for the treatment of COVID-19, comprising:
   a plurality of solid oral dosage forms of a first anti-viral agent consisting of a picornavirus 3C protease inhibitor,
   a plurality of solid oral dosage forms of a second anti-viral agent having a different mechanism of action consisting of ritonavir or a pharmaceutically acceptable salt thereof, and
   at least one additional anti-viral agent selected from the group consisting of dexamethasone and remdesivir.

8. The kit of claim 7, wherein the picornavirus 3C protease inhibitor is rupintrivir or a pharmaceutically acceptable salt thereof.

9. The kit of claim 7, wherein the solid oral dosage forms are provided for administration twice every 24 hours.

10. The kit of claim 7, wherein the solid oral dosage forms are provided for administration for an interval of five days to ten days.

11. The kit of claim 7, wherein the solid oral dosage forms are provided in a blister pack.

12. A method of treating COVID-19, the method comprising the step of administering to a patient a therapeutically effective amount of a first anti-viral agent consisting of a picornavirus 3C protease inhibitor or a pharmaceutically acceptable salt thereof, and a therapeutically effective amount of a second anti-viral agent having a different mechanism of action consisting of ritonavir or a pharmaceutically acceptable salt thereof.

13. The method of claim 12, wherein the picornavirus 3C protease inhibitor is rupintrivir or a pharmaceutically acceptable salt thereof.

14. The method of claim 12 further comprising the administration of one or more additional anti-viral drugs selected from the group consisting of phosphatidylserine modulators, entry inhibitors, protease inhibitors, RNA-dependent RNA polymerase inhibitors, and endosome acidifiers.

15. The method of claim 14, wherein the one or more additional anti-viral agent comprises dexamethasone.

16. The method of claim 14, wherein the one or more additional anti-viral agent comprises remdesivir.

17. The method of claim 12, wherein the first and second anti-viral agents are co-administered orally to the patient.

18. The method of claim 17, wherein about 100 mg to about 1500 mg of the first anti-viral agent and about 100 mg to about 1000 mg of the second anti-viral agent are co-administered orally to the patient.

19. The method of claim 17, wherein about 150 mg to about 300 mg of the first anti-viral agent and about 100 mg of the second anti-viral agent are co-administered orally to the patient twice a day.

20. The method of claim 19, wherein the first anti-viral agent and the second anti-viral agent are co-administered orally to the patient for an interval of five days to ten days.

* * * * *